US009586883B2

(12) United States Patent
Wickens et al.

(10) Patent No.: US 9,586,883 B2
(45) Date of Patent: Mar. 7, 2017

(54) ALDEHYDE-SELECTIVE WACKER-TYPE OXIDATION OF UNBIASED ALKENES

(71) Applicant: CALIFORNIA INSTITUTE OF TECHNOLOGY, Pasadena, CA (US)

(72) Inventors: Zachary K. Wickens, Pasadena, CA (US); Bill Morandi, Pasadena, CA (US); Robert H. Grubbs, South Pasadena, CA (US); Kacper Skakuj, Durham, NC (US); Sarah M. Bronner, San Francisco, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 14/255,049

(22) Filed: Apr. 17, 2014

(65) Prior Publication Data
US 2014/0316149 A1 Oct. 23, 2014

Related U.S. Application Data

(60) Provisional application No. 61/814,007, filed on Apr. 19, 2013.

(51) Int. Cl.
C07C 45/34 (2006.01)
C07C 249/04 (2006.01)
C07C 253/00 (2006.01)
C07C 201/12 (2006.01)
C07C 205/44 (2006.01)
C07C 209/60 (2006.01)
C07C 213/00 (2006.01)
C07C 227/08 (2006.01)
C07C 51/373 (2006.01)
C07C 59/235 (2006.01)
C07C 211/48 (2006.01)
C07C 217/48 (2006.01)
C07D 301/22 (2006.01)

(52) U.S. Cl.
CPC ............ C07C 45/34 (2013.01); C07C 51/373 (2013.01); C07C 201/12 (2013.01); C07C 205/44 (2013.01); C07C 209/60 (2013.01); C07C 213/00 (2013.01); C07C 227/08 (2013.01); C07C 249/04 (2013.01); C07C 253/00 (2013.01); C07D 301/22 (2013.01)

(58) Field of Classification Search
CPC ..... C07C 45/34; C07C 249/04; C07C 253/00; C07C 201/12; C07C 205/44; C07C 209/60; C07C 213/00; C07C 227/08; C07C 51/373; C07C 59/235; C07C 211/48; C07C 217/48; C07D 301/22
See application file for complete search history.

(56) References Cited

U.S. PATENT DOCUMENTS 4,661,642 A 4/1987 Feringa
5,136,105 A * 8/1992 Wenzel .................. 568/478
5,506,363 A 4/1996 Grate et al.
2012/0172634 A1 7/2012 Dong et al.
2014/0194604 A1 7/2014 Morandi et al.

FOREIGN PATENT DOCUMENTS

EP 0395792 9/1995

OTHER PUBLICATIONS

Wickens et al., Angewandte Chemie Int. Ed, 2013, 52, 11257-11260.*
Andrews et al., "The Transition-Metal Nitro-Nitrosyl Redox Couple: Catalytic Oxidation of Olefins to Ketones", J. Am. Chem. Soc., 1981, 103(10), 2894-2896.
Beller et al., "Catalytic Markovnikov and Anti-Markovnikov Functionalization of Alkenes and Alkynes: Recent Developments and Trends", Angew. Chem. Int. Ed., 2004, 43(26), 3368-3398.
Bronner et al., "Formal Anti-Arkovnikov Hydroamination of Terminal Olefins", Chemical Science, 2013, 5, 101-106.
Chowdhury et al., "An Iron Catalyzed Regioselective Oxidation Of Terminal Alkenes to Aldehydes", Chem. Commun., 2012, 48, 5497-5499.
Clyne et al., "The Synthesis of 14-Membered Macrocyclic Ethers", Tetrahedron, 1999, 55(48), 13659-13682.
Conley et al., "Discovery, Applications, And Catalytic Mechanisms of Shvo's Catalyst", Chem. Rev., 2010, 110(4), 2294-2312.
Cornell et al., "Recent Progress in Wacker Oxidations: Moving Toward Molecular Oxygent as the Sole Oxidant", Inorg. Chem., 2007, 46(6), 1903-1909.
Dong et al., "Primary Alcohols from Terminal Olefins: Formal Anti-Markovnikov Hydration Via Triple Relay Catalysis", Science, 2011, 333(6049), 1609-1612.
Dong et al., "Palladium-Catalyzed Selective Anti-Markovnikov Oxidation of Allylic Esters", Angew. Chem. Int. Ed., 2013, 52, 1-6.
Eilbracht et al., "Tandem Reaction Sequences Under Hydroformylation Conditions: New Synthetic Applications of Transition Metal Catalysis", Chem. Rev., 1999, 99(11), 3329-3365.
Feringa, "Catalytic Oxidation of Alk-1-enes to Aldehydes", J. Chem. Soc., 1986, 909-910.
Fischetti et al., "The Mechanism of Reactions of Organopalladium Salts with Vinylcyclopropanes", J. Organomet. Chem., 1985, 293(3), 391-405.
Friestad et al., "Aldehyde-Selective Wacker Oxidation in a Thiyl-Mediated Vinyl Group Transfer Route to Daunosamine", Org. Lett., 2007, 9(5), 777-780.
Ghosh et al., "Cu(II)-Catalyzed Olefin Migration and Prins Cyclization: Highly Diastereoselective Synthesis of Substitute Tetrahydropyrans", Org. Lett., 2011, 13(16), 4328-4331.
Gooch, "Moving Past Markovnikov's Rule", J. Chem. Educ., 2001, 78(10), 1358.
Gorczynski et al., "Activation of Peroxisome Proliferator-Activated Receptor γ (PPARγ) by Nitroalkene Fatty Acids: Importance of Nitration Position and Degree of Unsaturation", J. Med. Chem., 2009, 52(15), 4631-4639.
Haggin, "Chemists Seek Greater Recognition for Catalysis", Chem. Eng. News, 1993, 71, 23-27.

(Continued)

Primary Examiner — Sun Jae Yoo
(74) Attorney, Agent, or Firm — Baker & Hostetler LLP

(57) ABSTRACT

This disclosure is directed to methods of preparing organic aldehydes, each method comprising contacting a terminal olefin with an oxidizing mixture comprising:
(a) a dichloro-palladium complex;
(b) a copper complex;
(c) a source of nitrite;
under aerobic reaction conditions sufficient to convert at least a portion of the terminal olefin to an aldehyde.

15 Claims, 7 Drawing Sheets

(56) References Cited

OTHER PUBLICATIONS

Hintermann, "Recent Developments in Metal-Catalyzed Additions of Oxygen Nucleophiles to Alkenes and Alkynes", Topics in Organomet. Chem., 2010, 31, 123-155.
Hosokawa et al., "Palladium(II)_catalyzed Oxidation of Carbon-Carbon double bonds of Allylic Compounds with Molecular Oxygen; Regioselective Formation of Aldehydes", J. Chem. Soc., Chem. Commun., 1991, 21, 1559-1560.
Jira, "Acetaldehyde from Ethylene—A Retrospective on the Discovery of the Wacker Process", Angew. Chem. Int. Ed., 2009, 48(48), 9034-9037.
Kharasch et al., "Addition of Carbon Tetrachloride and Chloroform to Olefins", Science, 1945, 102(2640), 128.
Lai et al., "Reversal of Regiochemistry of Wacker-Type Reactions Oriented by Heteroatoms", J. Org. Chem., 1992, 57(12), 3485-3487.
López et al., "Regio- and Enantioselective Iridium-Catalyzed Intermolecular Allylic Etherification of Achiral Allylic Carbonates with Phenoxides", J. Am. Chem. Soc., 2003, 125(12), 3426-3427.
Mahatthananchai et al., "Catalytic Selective Synthesis", Angew. Chem. Int. Ed., 2012, 51, 10954-10990.
Maity et al., "Efficient and Stereoselective Nitration of Mono- and Disubstituted Olefins with $AgNO_2$ and TEMPO", J. Am. Chem. Soc., 2013, 135(9), 3355-3358.
Michel et al., "Catalyst-Controlled Wacker-Type Oxidation of Protected Allylic Amines", Angew. Chem. Int. Ed., 2010, 49, 7312-7315.
Michel et al., "A General and Efficient Catalyst System for a Wacker-Type Oxidation Using TBHP as the Terminal Oxidant: Application to Classically Challenging Substrates", J. Am. Chem. Soc., 2009, 131(17), 6076-6077.
Müller et al., "Hydroamination: Direct Addition of Amines to Alkenes and Alkynes", Chem. Rev., 2008, 108(9), 3795-3892.
Muzart, "Aldehydes from Pd-Catalysed Oxidation of Terminal Olefins", Tetrahedron, 2007, 63(32), 7505-7521.
Nagano et al., "Combined Lewis Acid Catalysts in Shotgun Process: A Convenient Synthesis of the Female Sex Pheromone of the Red-Bollworm Moth", Tetrahedron, 2002, 58(41), 8211-8217.
Raghavan et al., "An Efficient Stereoselective Synthesis of Penaresidin A from (E)-2-Protected Amino-3,4-unsatured Sulfoxide", J. Org. Chem., 2010, 75, 748-761.
Ritter et al., "A Standard System of Characterization for Olefin Metathesis Catalysts", Organometallics, 2006, 25(24), 5740-5745.
Seayad et al., "Internal Olefins to Linear Amines", Science, 2002, 297(5587), 1676-1678.
Sig man et al., "Imparting Catalyst Control Upon Classical Palladium-Catalyzed Alkenyl C—H Bond Functionalization Reactions", Acc. Chem. Res., 2012, 45(6), 874-884.
Smidt et al., "Katalytische Umsetzungen von Olefinen an Platinmetall-Verbindungen", Angew. Chem. Int., 1959, 71(5), 176-182, with English Abstract.
Stowers et al., "Nitrate as a Redox Co-Catalyst for the Aerobic Pd-Catalyzed Oxidation of Unactivated $sp^3$-C—H Bonds", Chem. Sci., 2012, 3, 3192-3195.
Teo et al., "Efficient and Highly Aldehyde Selective Wacker Oxidation", Organic Letters, 2012, 14:13, 3237-3239.
Trost, "On Inventing Reactions for Atom Economy", Acc.Chem. Res., 2002, 35(9), 695-705.
Tsuji et al., "A General Synthetic Method for the Preparation of Metyl Ketones From Terminal Olefins: 2-Decanone", Organic Syntheses, 1984, 62, 9.
Tsuj, "Synthethic Applications of the Palladium-Catalyzed Oxidation of Olefins to Keytones", Synthesis, 1984, 369-384.
Wang et al., "A Versatile Catalyst for Reductive Amination by Transfer Hydrogenation", Angew. Chem. Int. Ed., 2010, 49, 7548-7552.
Wang et al., "Pd(II)-Catalyzed Hydroxyl-Directed C—H Activation/C—O Cyclization: Expedient Construction of Dihydrobenzofurans", J. Am. Chem. Soc., 2010, 132(35), 12203-12205.
Weiner et al., "Aldehyde Selective Wacker Oxidations of Phthalimide Protected Allylic Amines: A New Catalytic Route to $\beta^3$-Amino Acids", J. Am. Chem. Soc., 2009, 131, 9473-9474.
Wenzel, "Cationic Palladium Nitro Complexes as Catalysts for the Oxygen-based Oxidation of Alkenes to Ketones, and for the Oxydehydrogenation of Ketones and Aldehydes to the—Unsaturated Analogues", J. Chem. Soc., Chem. Commun., 1989, 932-933.
Wenzel, "Oxidation of Olefins to Aldehydes Using A Palladium-Copper Catalyst", J. Chem. Soc., 1993, 862-864.
Wickens et al., "Aldehyde-Selective Wacker-Type Oxidation of Unbiased Alkenes Enabled by a Nitrite Co-Catalyst", Angew. Chem. Int. Ed., 2013, 52, 11257-11260.
Wickens et al., "Catalyst-Controlled Wacker-Type Oxidation: Facile Access to Functionalized Aldehydes", J. Am. Chem. Soc., 2014, 136, 890-893.
Wickens et al., "Catalyst-Controlled Wacker-Type Oxidation: Facile Access to Functionalized Aldehydes", Organic Letters, 2012, 14, 5728-5731.
Tseng et al., "A Modular Synthesis of Salvileucalin B. Structural Domaines", Org. Lett., 2011, 13(16), 4410-4413.
Anderson et al., "Experimental and Computational Study of a Direct OrCoupled Wacker Oxidation: Water Dependence in the Absence of Cu Salts", J. Am. Chem. Soc., 2010, 132(34), 11872-11874.
Backvall et al., "Stereo- and Regioselective Palladium-Catalyzed 1,4-Diacetoxylation of 1,3-Dienes", J. Org. Chem., Nov. 1984, 49, 4619-4631.
Backvall et al., "Biomimetic Adrobic 1,4-Oxidation of 1,3-Dienes Catalyzed by Cobalt Tetraphenylporphyrin-Hydroquinone-Palladium(II). An Example of Triple Catalysis", J. Am. Chem. Soc., Jul. 1987, 109(15), 4750-4752.
Backvall et al., "Multi-Step Catalysis for the Oxidation of Oleftns to Ketones by Molecular Oxygen in Chloride Free Media", Tetrahedron Letters, 1988, 29(23), 2885-2888.
Backvall et al., "Multistep Electron Transfer in Palladium-Catalyzed Aerobic Oxidations via a Metal Macrocycle-Quinone System", J. Am. Chem. Soc., Jun. 1990, 112, 5160-5166.
Beller, "A Personal View on Homogeneous Catalysis and its Perspectives for the Use of Renewables", Eur. J. Lipid Sci. Technol., 2008, 110(9), 789-796, Publication Online: Aug. 21, 2008.
Beller et al., "Catalytic Markovnikov and Anti-Markovnikov Functionalization of Alkenes and Alkynes: Recent Developments and Trends", Angew. Chem. Int. Ed., 2004, 43(26), 3368-3398, Published Online: Jun. 22, 2004.
Campbell et al., "Overcoming the 'Oxidant Problem': Strategies to Use O2 as the Oxidant in Organometallic C—H Oxidation Reactions Catalyzed by Pd (and Cu)", Ace. Chem. Res., 2012, 45(6), 851-863, Publication Online: Jan. 23, 2012.
Caterina et al., "The Capsaicin Receptor: A Heat-Activated ion Channel in the Pain Pathway", Nature, Oct. 23, 1997, 389, 816-824.
Chen et al., "Discovery And Characterization Of A Potent and Selective Antagonist Of Melanin-Concentrating Hormone Receptor 2", Biorg. Med. Chem Lett., 2012, 22, 363-366.
Chen et al, "Serial Ligand Catalysis: A Highly Selective Allylic C—H Oxidation", J. Am. Chem. Soc., 2005, 127, 6970-6971.
Carma et al., "Chemical Routes for the Transformation of Biomass into Chemicals", Chem. Rev., 2007, 107(6), 2411-2502.
Cornell et al., Discovery of a Practical Direct OrCoupled Wacker Oxidation with Pd[(−)-sparteine]Cl/, Org. Lett., 2006, 8(18), 4117-4120.
Decharin et al., "Benzoquinone-Promoted Reaction of $O_2$ with a $Pd^{II}$-Hydridge", J. Am. Chem. Soc., 2011, 133(15), 5732-5735.
Dong et al, "Palladium-Catalyzed Selective Anti-Markovnikov Oxidation of Allylic Esters", Angw. Chem., May 2013, 125(21), 5671-5675.
Dounay et al., "Total Synthesis of the Styrchnos Alkaloid (+)-Minfiensine: Tandem Enantioselective Intramolecular Heck-Iminium ion Cyclization", J. Am. Chem. Soc., 2008, 130(15), 5368-5377, Publication Online: Feb. 28, 2008.
Fujiwara et al., "Direct C—H Functionalization of Quinones with Boronic Acids", J. Am. Chem. Soc., 2011, 133(10), 3292-3295, Publication Online: Feb. 22, 2011.

(56) References Cited

OTHER PUBLICATIONS

Gligorich et al., "Recent Advancements and Challenges of Palladium11-catalyzed Oxidation Reactions with Molecular Oxygen as the Sole Oxidant", Chem. Commun., 2009, 26, 3854-3867.
Grennberg et al., "Acid-Induced Transferomation of Palladium(O)-Benzoquinone Complexes to Palladium(II) and Hydroquinone", Organometallics, 1993, 12(5), 1790-1793.
Grubbs, Handbook of Metathesis, Wiley-VCH 2003, vol. 1, 16 pages.
Harrak et al., "Galacto-Configured Aminocyclitol Phytoceramides are Potent in Vivo Invariant Natural Killer T Cell Stimulators", J. Am. Chem. Soc., 2011, 133(31), 12079-12084, Publication Online: Jul. 5, 2011.
Hoover et al., "A Highly Practical Cooper(I)/TEMPO Catalyst System for Chemoselective Aerobic Oxidation of Primary Alcohols", J. Am. Chem. Soc. 2011, 133, 16901-16910.
Hudson et al., "Nosteroidal 2,3-Dihydroquinoline Glucocorticoid Receptor Agonists with Reduced PEPCK Activation", Bioorg. Med. Chem. Lett., 2011, 21(6), 1654-1657.
Hull et al., "Mechanism of Benzoquinone-Promoted Palladium-Catalyzed Oxidative Cross-Coupling Reactions", J. Am. Chem. Soc., 131(28), 2009, 9651-9653, Publication Online: Jul. 1, 2009.
Ito et al., "Induction of Apoptosis in Leukemic Cells by Homovanillic Acid Derivative, Capsaicin, Through Oxidative Stress", Cancer Research, 2004, 64, 1071.
Kissin, "Vanilloid-Induced Conduction Analgesia: Selective, Dose-Dependent, Long-Lasting, with a Low Level of Potential Neurotoxicity", Anesth. Analg., 2008, 107(1), 271-281.
Kwong et al., "A General, Efficient, and Inexpensive Catalyst System for the Coupling of Aryl Iodides and Thiols", Org. Lett., 2002, 4(20), 3517-3520, Publication Online: Sep. 11, 2002.
Lee et al., "A Facile and Efficient Synthesis of 4-hydroxy-2,6-cis-tetrahydropyrans via Tandem Cross-Metathesis/Thermal S(N)2' Reaction: Protecting-Group-Free Synthesis of (+/−)-diospongin A.", Org. Lett., 2009, 11(22), 5202-5205.
Liu et al., "Highly Regioselective Pd-Catalyzed Intermolecular Aminoacetoxylation of Alkenes and Evidence for cis-Aminopalladation and SN2 C—O Bond Formation", J. Am. Chem. Soc., 2006, 128(22), 7179-7181.
Martinez et al., "Palladium-Catalyzed Vicinal Difunctionalization of Internal Alkenes: Diastereoselective Synethesis of Diamines", Angew. Chem. Int. Ed., 2012, 51(28), 7031-7034.
Miller et al., "Electrode-Mediated Wacker Oxidation of Cyclic and Internal Olefins", Can. J. Chem., 1992, 70(9), 2485-2490.
Miller, D.G. and Wayner, D.D., "Improved Method for the Wacker Oxidation of Cyclic and Internal Olefins", J. Org. Chem., 1990, 55(9), 2924-2927.
Mitsudome et al., "Convenient and Efficient Pd-Catalyzed Regioselective Oxyfunctionalization of Terminal Olefins by Using Molecular Oxygen as Sole Reoxidant", Angew. Chem. Int. Ed., 2006, 45(3), 481-485.
Mitsudome et al., "Convenient and Efficient Pd-Catalyzed Regioselective Oxyfunctionalization of Terminal Olefins by Using Molecular Oxygen as Sole Reoxidant", Angew. Chem. 2006, 118, 495-499.
Mitsudome et al, "Highly Atom-Efficient Oxidation of Electron-Deficient Internal Olefins to Ketones Using a Palladium Catalyst", Angew. Chem. Int. Ed., Apr. 22, 2013, 52, 5961-5964.
Mitsudome et al, "Simple and Clean Synthesis of Ketones From Internal Olefins Using PdCl2/N,N-dimethylacetamide Catalyst System", Tetrahedron Letters, 54, Jan. 17, 2013, 1596-1598.
Mitsudome et al, "Wacker-Type Oxidation of Internal Olefins Using a PdCl2/N,Ndimethylacetamide Catalyst System under Copper-Free Reaction Conditions", Angew. Chem. Int. Ed., 2010, 49, 1238-1240, published online: Dec. 28, 2009.
Morandi et al, "Regioselective Wacker Oxidation of Internal Alkenes: Rapid Access to Functionalized Ketones Facilitated by Cross-Metathesis", Angew. Chem. Int. Ed., Jul. 26, 2013, 52, 9751-9754.
Mori et al., "Capsaicin, a Component of Red Peppers, Inhibits the Growth of Androgen-Independent, p53 Mutant Prostate Cancer Cells", Cancer Res., Mar. 15, 2006, 66, 3222-3229.
Mukherjee et al., "A Diversity-Oriented Synthesis of Bicyclice cis-Dihydroarenediols, cis-4-Hydroxyscytalones, and Bicyclic Conduritol Analogues", Org. Lett., 2010, 12(11), 2472-2475, Publication Online: May 5, 2010.
Narute et al., "A [Pd]-Mediated w-alkynone ycloisomerization Approach for the Central Tetrahydropyran Unit and the Synthesis of C(31)-C(48) Fragment of Aflastatin A", Org. Biomol. Chem., 2011, 9, 5469-5475.
Piera, J. and Backvall, J.E., "Catalytic Oxidation of Organic Substrates by Molecular Oxygen and Hydrogen Peroxide by Multistep Electron Transfer-A Biomimetic Approach", Angew. Chem. Int. Ed. Apr. 28, 2008, 47, 3506-3523.
Raffier et al., "Desymmetrization of Hepta-1,6-dien-4-ol by Prins Reaction and Subsequent Cross-Metathesis: Access to Diospongine A Homologues", Synthesis, 2011, 24, 4037-4044.
Sato et al., "Asymmetric Cyclization of w-Formyl-1,3-Dienes Catalyzed by a Zerovalent Nickel Complex in the Presence of Silanes", J. Org. Chem., 2002, 67(26), 9310-9317.
Stahl, S., Cover Picture, Angewandte Chem., 2004, 116, 3480.
Stahl, "Palladium Oxidase Catalysis: Selective Oxidation of Organic Chemicals by Direct Dioxygen-Coupled Turnover", Angew. Chem. Inti. Ed., 2004, 43(26), 3400-3420, Jun. 28, 2004.
Steilmann et al, "Formation Of 2-Phenylethanol From Styrene In The Presence Of Zeolites And Uv Irradiation", Chem. Commun. Mar. 1999, 697-698.
Sun et al., "Nonpeptidic and Potent Small-Molecule Inhibitors of ciAP-1/2 and XIAP Proteins", J. Med. Chem, 2010, 53(17), 6361-6367, Publication Online: Aug. 4, 2010.
Trost et al., "Synthetic Strageies to Acetogenins. They hydroxybutenolide Terminus", Tetrahedron Lett., 1995, 36(34), 6021-6024.
Wang et al., "Supercritical Carbon Dioxide and Poly(Ethylene Glycol): An Environmentally Benign Biphasic Solvent System for Aerobic Oxidation of Styrene", Green Chem., 2007, 9, 882-887.
Wang et al., "Palladium-Catalyzed Direct Oxidation of Alkenes with Molecular Oxygen: General and Practical Methods for the Preparation of 1,2-Diols, Aldehydes, and Ketones", J. Org. Chem., 2010, 75(7), 2321-2326.
Zhou et al., "A General and Convenient Catalytic Synthesis of Nitriles from Amides and Silanes", Org. Lett. 2009, 11(11), 2461-2464.

\* cited by examiner

A. Unbiased Alkenes: Natural Wacker Selectivity

B. Biased Alkenes: a Substrate-Controlled Strategy

C. Unbiased Alkenes: Reversed Wacker Selectivity (Our Goal)

FIG. 3B-C

B. Stoichiometric experiments

C. Ag⁺ or NO₂⁻ key co-catalyst?

B. Key Stoichiometric ¹⁸O-Labeling

FIG. 6

| | allylic | homoallylic | unfunctionalized |
|---|---|---|---|
| | ⩘⩘⩘OPh | ⩘⩘⩘⩘OPh | ⩘⩘⩘⩘C$_8$H$_{17}$ |
| Relative rate: | 2.4 | 2.8 | 1.0 |

FIG. 7

X–C$_6$H$_4$–O–(CH$_2$)$_n$–CH=CH$_2$ →[PdCl$_2$(PhCN)$_2$, CuCl$_2$, NaNO$_2$ / t-BuOH/MeNO$_2$ (15:1), O$_2$ (1 atm), RT]→ X–C$_6$H$_4$–O–(CH$_2$)$_n$–CH$_2$CHO

| | | X = NO$_2$ | X = H | X = OMe |
|---|---|---|---|---|
| n = 1 (allylic) | Selectivity | 97:3 | 97:3 | 96:4 |
| | Relative rate | 1.2 | 1.0 | 1.2 |
| n = 2 (homoallylic) | Selectivity | 90:10 | 91:9 | 90:10 |
| | Relative rate | 1.3 | 1.0 | 1.1 |

ALDEHYDE-SELECTIVE WACKER-TYPE OXIDATION OF UNBIASED ALKENES

CROSS REFERENCE TO RELATED APPLICATIONS

This application claims priority to U.S. Patent Application Ser. No. 61/814,007, filed Apr. 19, 2013, the contents of which is incorporated by reference herein for all purposes.

GOVERNMENT RIGHTS

This invention was made with government support under Grant No. GM068825 and Grant No. GM102984 awarded by the National Institutes of Health. The Government has certain rights in the invention.

TECHNICAL FIELD

This disclosure involves the catalytic transformation of terminal olefins to aldehydes, including the formation of aldehydes from unbiased olefins

BACKGROUND

The efficient catalytic transformation of monosubstituted alkenes into valuable terminally functionalized alkanes, such as amines, alcohols, acids and aldehydes, is of critical importance to polymer science, drug discovery, chemical biology and the bulk chemical industry. However, these transformations require breaking a textbook rule of organic chemistry: Markovnikov's rule. This rule predicts that nucleophiles will attack the more substituted carbon of an alkene. Thus, to functionalize the terminal position of unbiased alkenes with an oxygen or nitrogen nucleophile, the innate (substrate-controlled) Markovnikov selectivity must be superseded using a highly anti-Markovnikov selective catalyst-controlled process. To date, only a handful of reactions have achieved catalytic intermolecular anti-Markovnikov installation of oxygen or nitrogen. These examples have nearly all required biased substrates (such as styrenes or conjugate acceptors) to efficiently obtain anti-Markovnikov selectivity. Despite the recognition of such important transformations as top challenges in catalysis two decades ago, no synthetically useful direct, catalytic anti-Markovnikov addition of oxygen or nitrogen to unbiased alkenes has been realized to date.

The traditional approach to anti-Markovnikov functionalization of terminal alkenes has relied upon the ubiquitous hydroboration reaction (11). The wide adoption of hydroboration in organic synthesis is due to the synthetic versatility of the alkylborane products, which can be transformed into many important functionalities. Unfortunately, this stoichiometric process generates significant waste and has limited functional-group compatibility.

SUMMARY

Certain embodiments of this invention provide methods of preparing organic aldehydes, each method comprising contacting a terminal olefin with an oxidizing mixture comprising:
(a) a dichloro-palladium complex;
(b) a copper complex;
(c) a source of nitrite;
under aerobic reaction conditions sufficient to convert at least a portion of the terminal olefin to an aldehyde. Within these embodiments are those which describe various preferred types of palladium and copper complexes, nitrite sources (inorganic and organic sources), temperature and aerobic compositions, the nature of the substrate terminal olefins, and the conversion and selectivity available from said methods.

In some embodiments, the methods comprise contacting a terminal olefin with an oxidizing mixture comprising (or, alternatively, resulting from the room temperature mixing of):
(a) bis(acetonitrile)dichloro-palladium(II) or bis(benzonitrile)dichloro-palladium(II);
(b) a copper source comprising $CuCl_2$, CuCl, or $CuCl_2.2H_2O$;
(c) a nitrite source comprising $AgNO_2$ or $NaNO_2$;
dissolved or dispersed in a tert-butanol:nitromethane (15:1 vol/vol) solvent;
under an air or oxygen atmosphere at a pressure of from about 1 to about 3 atmospheres at a temperatures in a range of from 15° C. to about 35° C., preferably 20° C. to about 25° C. for a period of time in a range of from about 1 to about 48 hours so as to convert at least a portion of the terminal olefin to an aldehyde with a selectivity of at least 80% aldehyde, preferably at least 90% aldehyde.

Other embodiments provide for the compositions useful for affecting these transformations.

Still other embodiments provide methods of converting terminal olefins to other functional groups. For example, some embodiments provide methods of converting a terminal olefin to an acetal, acylal, terminal alcohol, $\alpha,\beta$-unsaturated aldehyde, aldoxime, anhydride, amide, amine, $\alpha$-amino nitrile, carboxylic acid, carboxylate ester, $\alpha,\beta$-unsaturated carboxylic acid, 1,3 diol, epoxide, $\alpha,\beta$-unsaturated epoxy ester, $\beta$-hydroxyester, $\alpha$-hydroxy nitrile, hydrazone, nitrile, $\beta$-nitro alcohol, semicarbazone, halide, gem-dihalide, or $\alpha$-halo ether, each method comprising
(a) converting the terminal olefin to a terminal aldehyde according to the aldehyde-forming methods described herein; and
(b) converting the terminal aldehyde to the acetal, acylal, terminal alcohol, $\alpha,\beta$-unsaturated aldehyde, aldoxime, anhydride, amide, amine, $\alpha$-amino nitrile, carboxylic acid, carboxylate ester, $\alpha,\beta$-unsaturated carboxylic acid, 1,3 diol, epoxide, $\alpha,\beta$-unsaturated epoxy ester, $\beta$-hydroxyester, $\alpha$-hydroxy nitrile, hydrazone, nitrile, $\beta$-nitro alcohol, semicarbazone, halide, gem-dihalide, or $\alpha$-halo ether.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In addition, the drawings are not necessarily drawn to scale. In the drawings.

Figure 3A:
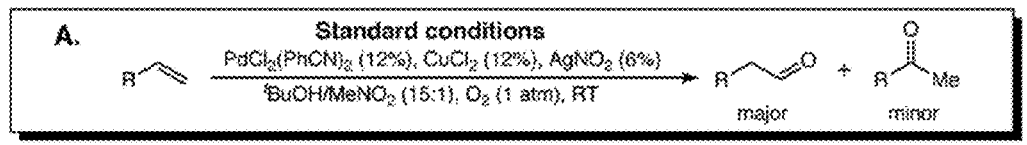
Figure 3A:
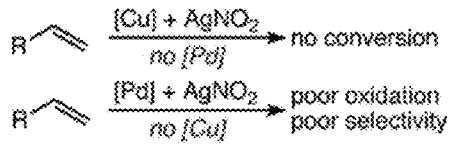
Figure 3A:
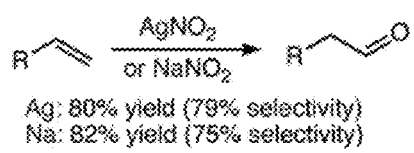
Figure 3D:
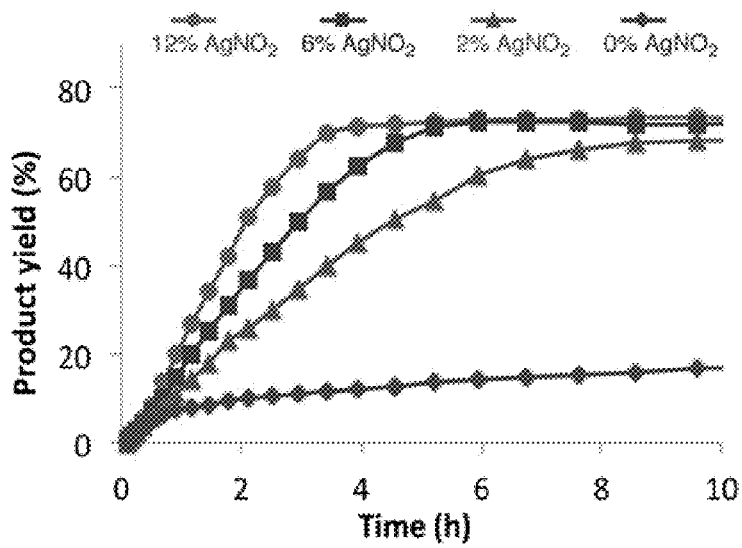
Figure 3E:
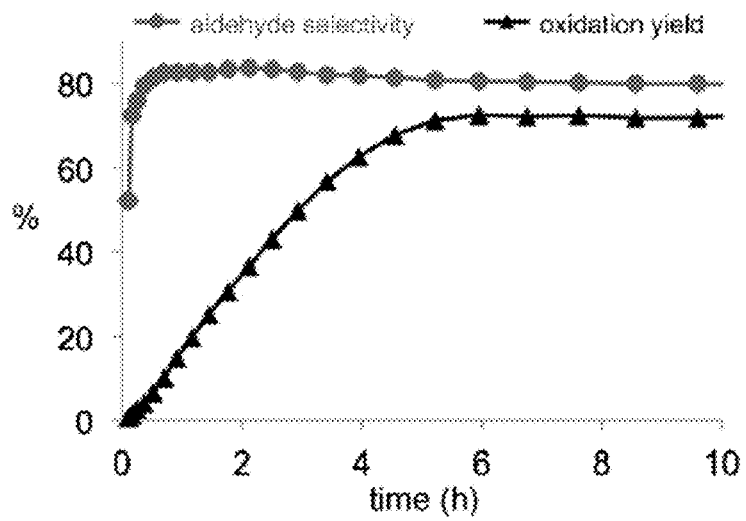

FIG. 3A shows standard optimized conditions for aldehyde-selective Wacker. FIG. 3B shows stoichiometric control experiments. FIG. 3C shows replacement of AgNO$_2$ with NaNO$_2$. FIG. 3D shows reaction profiles using 12, 6, 2 and 0 mol % AgNO$_2$. FIG. 3E shows reaction profile of nitrite-modified Wacker oxidation of 1-dodecene to assess stability of aldehyde-selective catalytically active species.

Figure 4:
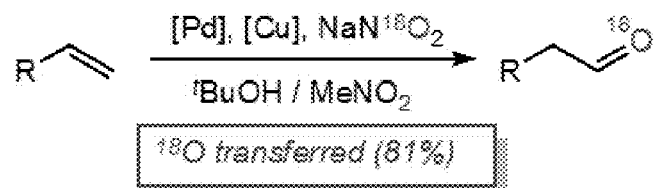

FIG. 4 shows results the of stoichiometric $^{18}$O-labeling experiment demonstrates aldehydic oxygen is derived from nitrite.

Figure 5A:
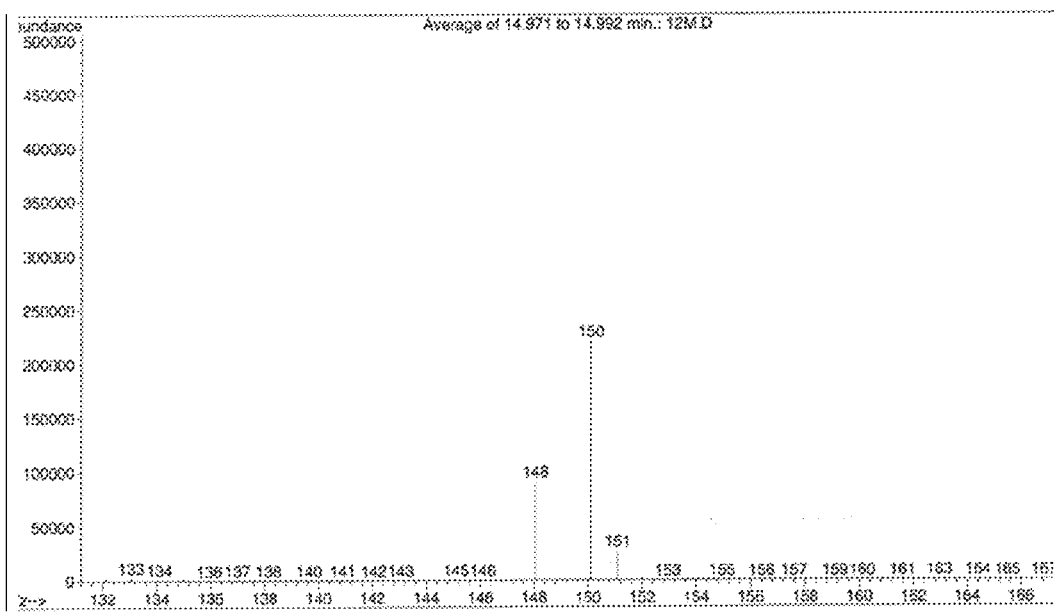
Figure 5B:
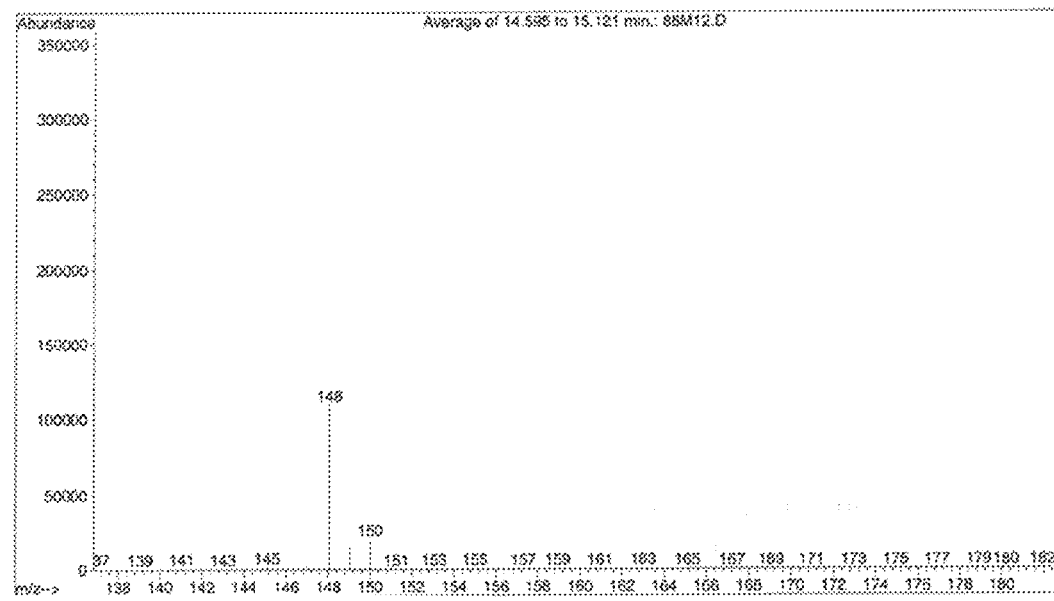

FIG. 5A shows mass spectral data for $^{18}$O-enriched 4-phenylbutanal and FIG. 5B shows analogous data for the product obtained from enrichment control experiments, as described in Example 3.1.6.

FIG. 6 shows the relative rates of oxidation to aldehyde as a function of substrate under nitrite-modified Wacker conditions, as described in Example 4.3. See Table 5 for conditions.

FIG. 7 shows selectivity and relative rates of oxidation to aldehyde as a function of substrate's electronic properties under nitrite-modified Wacker conditions (see Table 5 for conditions; 10 min reaction time), as described in Example 4.3.

Figure 8:
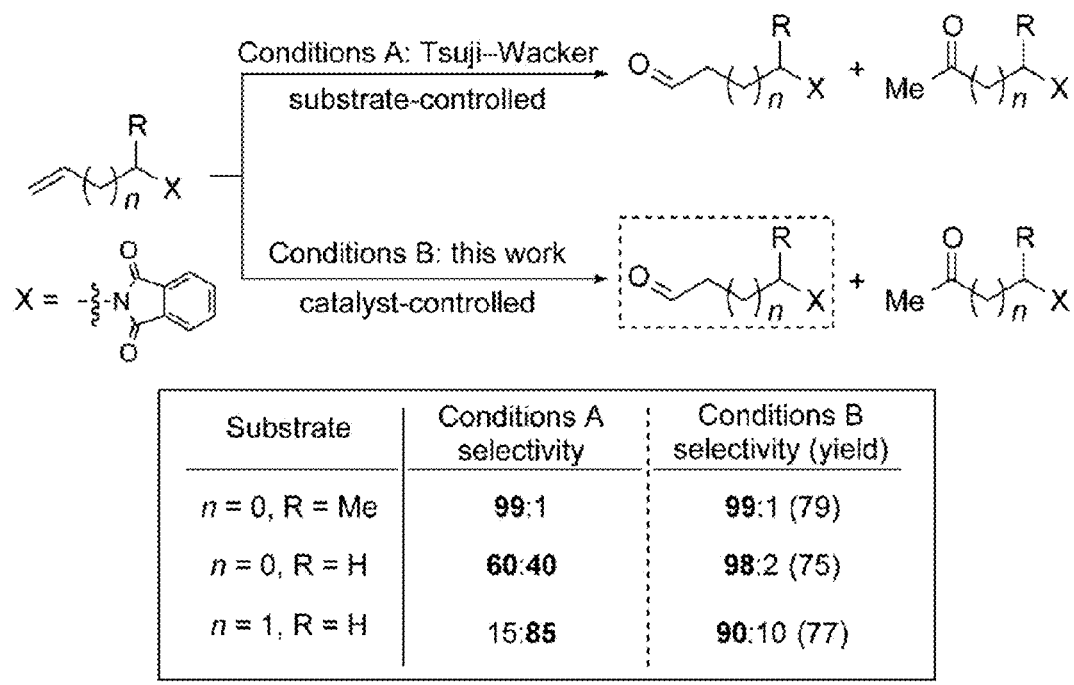

FIG. 8 shows a comparison of innate Wacker selectivity (conditions A) to catalyst controlled selectivity (conditions B). Conditions A: PdCl$_2$ (10-30 mol %), CuCl (1 equiv), DMF/H$_2$O (7:1), RT, O$_2$ (1 atm). Conditions B: alkene (0.5 mmol), [PdCl$_2$(PhCN)$_2$] (12 mol %), CuCl$_2$ (12 mol %), AgNO$_2$ (6 mol %), tert-BuOH/MeNO$_2$ (15:1), RT, O$_2$ (1 atm). Aldehyde yields determined after purification. Selectivity determined by $^1$H NMR analysis prior to purification.

DETAILED DESCRIPTION OF ILLUSTRATIVE EMBODIMENTS

The efficient catalytic transformation of monosubstituted alkenes into valuable terminally functionalized alkanes is of wide importance to the molecular sciences. The lack of an efficient catalytic methodology is exemplified by the current use of stoichiometric transformations such as the hydroboration reaction. An aerobic oxidation of unbiased alkenes to aldehydes would offer a catalytic entry into anti-Markovnikov functionalization of alkenes, as aldehydes are highly versatile synthetic intermediates.

The present disclosure describes a catalytic system that provides the first example of efficient reversal of the Markovnikov selectivity in a Wacker-type oxidation of unbiased olefins. Up to 80% yield and as high as 90% aldehyde-selectivity can be obtained from aliphatic alkenes and several functional groups are tolerated. This aldehyde-selective oxidation provides direct access to the valuable aldehydes and derivatives which can be derived therefrom.

The present invention may be understood more readily by reference to the following description taken in connection with the accompanying Figures and Examples, all of which form a part of this disclosure. It is to be understood that this invention is not limited to the specific products, methods, conditions or parameters described or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer to compositions and methods of making and using said compositions. That is, where the disclosure describes or claims a feature or embodiment associated with a composition or a method of making or using a composition, it is appreciated that such a description or claim is intended to extend these features or embodiment to embodiments in each of these contexts (i.e., compositions, methods of making, and methods of using).

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

The transitional terms "comprising," "consisting essentially of," and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of" and "consisting essentially of" For those embodiments provided in terms of "consisting essentially of," the basic and novel characteristic(s) is the operability of the methods (or the systems used in such methods or the compositions derived therefrom) as a transition metal-free method of effecting the reductive cleavage of C—O, C—N, or C—S bonds.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

Throughout this specification, words are to be afforded their normal meaning, as would be understood by those skilled in the relevant art. However, so as to avoid misunderstanding, the meanings of certain terms will be specifically defined or clarified.

The term "alkyl" as used herein refers to a linear, branched, or cyclic saturated hydrocarbon group typically although not necessarily containing 1 to about 24 carbon atoms, preferably 1 to about 12 carbon atoms, such as methyl, ethyl, n-propyl, isopropyl, n-butyl, isobutyl, tert-Butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of 1 to 6 carbon atoms, and the specific term "cycloalkyl" intends a cyclic alkyl group, typically having 4 to 8, preferably 5 to 7, carbon atoms. The term "substituted alkyl" refers to alkyl groups substituted with one or more substituent groups, and the terms "heteroatom-containing alkyl" and "heteroalkyl" refer to alkyl groups in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl groups, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl groups substituted with one or more substituent groups, and the terms "heteroatom-containing alkenyl" and "heteroalkenyl" refer to alkenyl groups in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl groups, respectively.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to about 24 carbon atoms containing at least one triple bond, such as ethynyl, n-propynyl, and the like. Preferred alkynyl groups herein contain 2 to about 12 carbon atoms. The term "lower alkynyl" intends an alkynyl group of 2 to 6 carbon atoms. The term "substituted alkynyl" refers to an alkynyl group substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include a linear, branched, unsubstituted, substituted, and/or heteroatom-containing alkynyl and lower alkynyl group, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aromatic" refers to the ring moieties which satisfy the Hückel 4n+2 rule for aromaticity, and includes both aryl (i.e., carbocyclic) and heteroaryl (also called heteroaromatic) structures, including aryl, aralkyl, alkaryl, heteroaryl, heteroaralkyl, or alk-heteroaryl moieties.

The term "aryl" as used herein, and unless otherwise specified, refers to an aromatic substituent or structure containing a single aromatic ring or multiple aromatic rings that are fused together, directly linked, or indirectly linked (such that the different aromatic rings are bound to a common group such as a methylene or ethylene moiety). Unless otherwise modified, the term "aryl" refers to carbocyclic structures. Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail infra.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 24 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms, and particularly preferred alkaryl and aralkyl groups contain 6 to 16 carbon atoms. Alkaryl groups include, for example, p-methylphenyl, 2,4-dimethylphenyl, p-cyclohexylphenyl, 2,7-dimethylnaphthyl, 7-cyclooctyl-naphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, or —(CO)-aralkyl, and the term "acyloxy" refers to substituents having the formula —O(CO)-alkyl, —O(CO)-aryl, or —O(CO)-aralkyl, wherein "alkyl," "aryl, and "aralkyl" are as defined above.

The terms "cyclic" and "ring" refer to alicyclic or aromatic groups that may or may not be substituted and/or heteroatom-containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic, or polycyclic. The term "acyclic" refers to a structure in which the double bond is not contained within a ring structure.

The terms "halo" and "halogen" are used in the conventional sense to refer to a chloro, bromo, fluoro, or iodo substituent.

The term "heteroatom-containing" as in a "heteroatom-containing group" refers to a hydrocarbon molecule or molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

By "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups referred to herein as "Fn," such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_1$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl ((CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO—), carbamoyl (—(CO)—$NH_2$), mono-($C_1$-$C_{24}$ alkyl)-substituted carbamoyl (—(CO)NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH($C_1$-$C_{24}$ alkyl)), di-($C_1$-$C_{24}$ haloalkyl)-substituted carbamoyl (—(CO)—N($C_1$-$C_{24}$ alkyl)$_2$), mono-($C_5$-$C_{24}$ aryl)-substituted carbamoyl (—(CO)—NH-aryl), di-($C_5$-$C_{24}$ aryl)substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl, thiocarbamoyl (—(CS)—$NH_2$), mono-($C_1$-$C_{24}$ alkyl)-substituted thiocarbamoyl (—(CO)—NH($C_1$-$C_{24}$ alkyl)), di-($C_1$-$C_{24}$ alkyl)-substituted thiocarbamoyl (—(CO)—N($C_1$-$C_{24}$ alkyl)$_2$), mono-($C_5$-$C_{24}$ aryl)substituted thiocarbamoyl (—(CO)—NH-aryl), di-($C_5$-$C_{24}$ aryl)-substituted thiocarbamoyl (—(CO)—N($C_5$-$C_{24}$ aryl)$_2$), di-N—($C_1$-$C_{24}$ alkyl), N—($C_5$-$C_{24}$ aryl)-substituted thiocarbamoyl, carbamido (—NH—(CO)—$NH_2$), cyano(—C≡N), cyanato (—O—C≡N), thiocyanato (—S—C≡N), formyl (—(CO)—H), thioformyl (—(CS)—H), amino (—$NH_2$), mono-($C_1$-$C_{24}$ alkyl)-substituted amino, di-($C_1$-$C_{24}$ alkyl)-substituted amino, mono-($C_5$-$C_{24}$ aryl)substituted amino, di-($C_5$-$C_{24}$ aryl)-substituted amino, $C_1$-$C_{24}$ alkylamido (—NH—(CO)-alkyl), $C_6$-$C_{24}$ arylamido (—NH—(CO)-aryl), imino (—CR=NH where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N(alkyl), where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—$NO_2$), nitroso (—NO), sulfo (—$SO_2OH$), sulfonate($SO_2O$—), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—$SO_2$-alkyl), $C_1$-$C_{24}$ monoalkylaminosulfonyl-$SO_2$—N(H)alkyl), $C_1$-$C_{24}$ dialkylaminosulfonyl-$SO_2$—N(alkyl)$_2$, $C_5$-$C_{24}$ arylsulfonyl (—$SO_2$-aryl), boryl (—$BH_2$), borono (—$B(OH)_2$), boronato (—$B(OR)_2$ where R is alkyl or aryl), phosphono (—P(O)(OH)$_2$), phosphonato (—P(O)(O)$_2$), phosphinato (P(O)(O—)), phospho (—$PO_2$), and phosphine (—$PH_2$); and the moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably $C_2$-$C_6$ alkynyl), $C_5$-$C_{24}$ aryl (preferably $C_5$-$C_{24}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

By "functionalized" as in "functionalized alkyl," "functionalized olefin," "functionalized cyclic olefin," and the like, is meant that in the alkyl, olefin, cyclic olefin, or other moiety, at least one hydrogen atom bound to a carbon (or other) atom is replaced with one or more functional groups such as those described herein and above. The term "functional group" is meant to include any functional species that is suitable for the uses described herein. In particular, as used herein, a functional group would necessarily possess the ability to react with or bond to corresponding functional groups on a substrate surface.

In addition, the aforementioned functional groups may, if a particular group permits, be further substituted with one or more additional functional groups such as those specifically enumerated above. Analogously, the above-mentioned groups may be further substituted with one or more functional groups such as those specifically enumerated.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The present invention includes methods of preparing organic aldehydes, each method comprising contacting a terminal olefin with an oxidizing mixture comprising (or resulting from the room temperature mixing of):

(a) a dichloro-palladium complex;
(b) a copper complex;
(c) a source of nitrite;

under aerobic reaction conditions sufficient to convert at least a portion of the terminal olefin to an aldehyde. The methods are highly selective for the formation of aldehydes, relative to the formation of ketones (either by direct formation or isomerization). The term "at least a portion of the terminal olefin to an aldehyde" is intended to connote that the resulting oxidized product comprises a least as much aldehyde as ketone (i.e., selectivity of 50% or more). In preferred embodiments, the methods produce products from the terminal olefin in which the conversion of the initial substrate to product is at least 70%, based on the amount of initial substrate, and the selectivity for aldehydes is at least 60% of the converted product, depending on the nature of the substrate. In some independent embodiments, the conversion is at least about 70%, at least about 75%, at least about 80%, at least about 85%, at least about 90%, and at least about 95% and the selectivity is at least about 65%, at least about 70%, at least about 75%, at least about 80%, at least about 85% at least about 90%, or at least about 95%. The term selectivity refers to the ratio of aldehyde product, relative to the total of aldehyde and ketone products. Selectivity is often defined in terms of produced aldehydes, but may also refer to isolated product.

The methods are catalytic independently with respect to the palladium, copper and nitrite, where catalytic is defined as having a turnover number greater than 1, 5, 10, 25, 50, or 100 with respect to each of these components. In this regard, it was found effective to operate the methods wherein the palladium is present in an amount in a range of from about 5 mol % to about 25 mol % relative to the amount of the substrate, preferably in a range of from about 5 mol % to about 15 mol %. These ranges are not intrinsic in the methods (which may operate with palladium concentrations much higher, for example where the palladium is present in an amount equivalent to the substrate), but reflect the economic attraction of using lesser amounts of expensive palladium materials. Similarly, the methods appear to work well, and certain embodiments include those where the copper is present in similar ranges, for example from about 5 mol % to about 25 mol % relative to the amount of the substrate, or in a range of from about 5 mol % to about 15 mol %. In preferred embodiments, the ratio of Pd:Cu is about 1:1, but may range from about 1.5:1 to about 1:1.5, or from about 1.2:1 to about 1:1.2, or from about 1.1:1 to about 1:1.1. Also, the methods appear to work well, and certain embodiments include those where the nitrite is present in an amount in a range of from about 2.5 mol % to about 12.5 mol % relative to the amount of the substrate, preferably in a range of from about 2.5 mol % to about 7.5 mol %. In preferred embodiments, the ratio of nitrite:Pd or nitrite or:Cu is about 0.5:1, but may range from about 1:1 to about 0.25:1, or from about 0.75:1 to about 0.38:1, or from about 0.4:1 to about 0.6:1.

The methods are catalytically active at mild temperatures, with good results being achieved even at ambient room temperature, but the methods are effective and within the scope of the present invention(s) where the temperatures of the reaction conditions are in a range of having a lower limit of about 10° C., about 15° C., about 20° C., about 25° C., about 30° C., and about 35° C. and an upper limit of about 80° C., about 70° C., about 60° C., about 50° C., about 40° C., about 35° C., about 30° C., or about 25° C. Further exemplary temperature ranges include from about 15° C. to about 35° C., from about 20° C. to about 30° C., or from about 20° C. to about 25° C.

Certain systems have been reported in the literature, for example so-called Tsuji-Wacker systems, but none of them have been able to achieve the conversion yields and selectivities of the present systems. While it is not entirely understood how the total system works, each features is considered to be important for performance. Removal of any of these components results in dramatically poorer conversion, selectivity, or both. In arriving at the present system(s), a fundamentally different thinking was applied to the mechanism of action and each of the reaction parameters were tested against this mechanistic model (see Examples herein).

In various embodiments, the palladium complex more broadly comprises a halo-palladium complex or a dihalo-palladium complex, for example a chloro-palladium or especially a dichloro-palladium complex comprising at least one organic nitrile or other neutral coordinating ligand—e.g., (organic nitrile)$_{4-x}$PdCl$_x$, where x is 1-3. The palladium complex may be cationic, neutral, or anionic, depending on the number of each of these ligands. Cationic and anionic complexes may also be referred to as palladium salts. Neutral dichloro-palladium complexes appear to be preferred, especially as the precursors of the reactions. For example, bis(nitrile)dichloro-palladium(II) complexes have been found to work especially well in the present methods (where the nitrile is an organic moiety resistant to oxidation under the described reaction conditions). In particular, bis (acetonitrile)dichloro-palladium(II) or bis(benzonitrile)dichloro-palladium(II) have shown excellent performance. In fact, these bis(nitrile)dichloro-palladium(II) complexes has been found to provide surprisingly better performance than palladium complexes having no chlorine ligands or other coordinating anionic ligands. For example, when Pd(trifluoroacetate)$_2$ or Pd(BF$_4$)$_2$ were used in place of dichloropalladium complexes, the methods yielded significant olefin isomerization and ketone selectivity. Similarly, the used of Pd(acetate)$_2$ and/or Cu(acetate)$_2$ instead of their dichloride counterparts resulted in low yields and ketone selectivity. The presence of nitrite ligands within the coordination sphere of the palladium complex appears to provide a deleterious effect on the reaction conversion and selectivity; when Pd(NO$_2$)Cl(MeCN)$_2$ was used in place of PdCl$_2$ (MeCN)$_2$, poor aldehyde selectivity was obtained (~1:1).

The nature of the copper salt is also important for the methods to work most effectively. Again, copper salts having associated halide ligands, especially chloride ligands, appear to be most effective. Such methods and systems may include those based specifically on added CuCl$_2$/CuCl/ CuCl$_2$.2H$_2$O systems, but may also include those where the copper halide or copper chloride association is generated in situ, for example by adding halide or chloride to copper nitrate, nitrite, or tetrafluoroborate. Removal of copper from the process yielded only traces of products. Exposure of alkene to stoichiometric palladium and silver nitrite, however, also provided incomplete oxidation and poor selectivity, suggesting a more intimate role of the copper salt than a simple redox catalyst for palladium (See Example 3.2). Furthermore, stoichiometric copper dichloride and silver nitrite (no palladium) provided no conversion of the alkene. Thus, it appears that both palladium and copper are crucial metals for the efficient stoichiometric oxidation of alkenes to aldehydes.

The methods thus far have been described in terms of a source of nitrite, especially free nitrite (as opposed to coordinated nitrite), which may include nitrite salts, organic nitrites, or a nitrosonium salts, but a broader characterization may include those materials also capable of reversibly forming oxygen-centered radicals under the conditions of the reaction. Oximes may also operate in this capacity. This explanation is consistent with the observation that nitrates do not affect the desired transformation and why palladium or copper nitrite complexes offer compromised performance when added as such, relative to the identified independent sources of nitrites, and these metal nitrites are less or non-preferred sources of nitrites in the described methods. That is, the term "source of nitrite" is intended to connote a separate source of free nitrite, that is not added as part of the coordination sphere of the palladium complex. Such is not to say that minor amounts of such species may be generated in situ during the course of the reaction, but these materials appear to be relatively poor sources of nitrite and show relatively poor selectivity to form aldehydes when added directly.

Instead, preferred nitrites salts include salts of an alkali metal, alkaline earth metal, or silver. $NaNO_2$ and $AgNO_2$ are preferred sources of nitrite. Interestingly, and for reasons not understood, $AgNO_2$ outperformed $NaNO_2$ when the substrates are unbiased olefins, whereas $NaNO_2$ appears to outperform $AgNO_2$ when the substrates contain directing groups (compare, e.g., Examples 3.2 and 4.3). Interestingly, when tetrabutylammonium nitrite was used in place of $AgNO_2$ or $NaNO_2$, the reactions resulted in low yields and poor selectivity (~2:1 ketone/aldehyde). It would appear that the polarizing effect of the harder metal center ($Na^+$ or $Ag^+$) may play an important, yet unidentified role, in the conversion and selectivity of the methods.

In other embodiments, the source of the nitrite may be organic nitrites or nitrosonium salts, such as $NOBF_4$. Attractive organic nitrites include $C_{1-6}$—ONO, for example n-BuONO, tert-BuONO, and tert-amyl-ONO (see Example 3.2).

From the studies described herein it is shown that co-catalytic nitrite salts were found to provide unparalleled reactivity in the presence of palladium and copper. Intriguingly, when the reaction was conducted in an open vessel, both yield and selectivity were significantly worse than when sealed under air. Clearly air/oxygen is at least a highly desirable if not a required element of the system. The methods are described in terms of operable under aerobic conditions, and those which encourage the presence of air/oxygen within the reaction environment are preferred; for example, operating the method with air/oxygen bubbling through the reaction mixture or conducting the methods under elevated air/oxygen pressure. Having said this, there appears to be a limit to the improvements seen in increasing the oxygen pressure, where increase in oxygen pressure above about 3 atm did not provide increased efficiency but did marginally increase the selectivity (see, e.g., Example 3.1.5).

The methods operate well in the presence of non-nucleophilic or poorly-nucleophilic solvents or solvent mixtures. The term "non-nucleophilic solvent" is one known to those skilled in the art; in the present case, it refers to a solvent is not a free primary or secondary alcohol or amine or an organic acid with pKa>3. "Poorly nucleophilic solvents" include those which may contain nucleophilic moieties, but which moieties are sterically or otherwise hindered. Preferably, the solvent is not one that would be reasonably expected to coordinate strongly to the palladium or copper complexes. Non-nucleophilic or poorly nucleophilic solvents can include ethers (e.g., glymes, tetrahydrofuran, 1,4-dioxane), which are capable of solubilizing both the oxidizing mixture and the substrate olefins. Preferred embodiments include those where the non-nucleophilic or poorly nucleophilic solvent or solvent mixture comprises tert-butanol (tert-BuOH). When secondary or primary alcohols (including even tert-Bu-$CH_2$—OH are used in place of tert-BuOH, the reaction methods yield primarily ketones. When structurally related tertiary alcohols (less hindered than tert-butanol), for example tert-amyl alcohol, are used in place of tert-BuOH, no significant reaction occurs in 8 hours. Even when the solvent comprises tert-butanol (tert-BuOH), the methods were found to proceed even better with the addition of highly polar, aprotic nitromethane, the latter solvent being present in an amount of from about 5 vol % to about 25 vol %, relative to the total solvent system. In some embodiments, the solvent mixture comprises or consists essentially of tert-butanol:nitromethane in a ratio of about 15 to 1 vol/vol. Variation of this ratio (e.g., 20:1, 18:1, 16:1, 14:1, 12:1, 10:1, 9.5:1, 8.5:1, 8:1, 7.5:1, or 7:1) may also be acceptable. The reason for this improvement is not known or predicted. The effect of the nitromethane solvent may be rationalized after-the-fact to provide some benefit of polarity, stabilization of some intermediate, or improvement in co-solvency of the oxidizing medium and substrates. Other co-solvents which improve one or more of these effects may also provide similar benefit.

Interestingly it has been observed in early efforts that using $PdCl_2$ and $CuCl_2$ in tert-butanol at 30° C. resulted in poor selectivity and yield either in the absence or presence (≥1 equiv.) of water. But if water was slowly added in a dry glovebox environment, good selectivity (5:1 aldehyde/ketone) could be obtained; unfortunately yields above 30% could not be obtained anyway using this very labor intensive, impractical process.

In more specific embodiments, the methods of preparing organic aldehydes include those where, each method comprising contacting a terminal olefin with an oxidizing mixture comprising (or resulting from the room temperature mixing of):

(a) bis(acetonitrile)dichloro-palladium(II) or bis(benzonitrile)dichloro-palladium(II);

(b) a copper source comprising $CuCl_2$, CuCl, or $CuCl_2.2H_2O$;

(c) a nitrite source comprising $AgNO_2$ or $NaNO_2$;

dissolved or dispersed in a tert-butanol:nitromethane (15:1 vol/vol) solvent;

under an air or oxygen atmosphere at a pressure of from about 1 to about 3 atmospheres at a temperatures in a range of from 15° C. to about 35° C., preferably 20° C. to about 25° C. for a period of time in a range of from about 1 to about 48 hours so as to convert at least a portion of the terminal olefin to an aldehyde with a selectivity of at least 80% aldehyde, preferably at least 90% aldehyde.

The methods are very forgiving with respect to the nature of other functional groups on the terminal olefin substrate and surprising in their selectivity for formation of aldehydes, even in unbiased terminal olefins. As used herein, the term "unbiased" refers to a terminal olefin comprising only C—C or C—H (or C-D) linkages within about 3 carbon units from the target terminal olefin, such that there are no groups which may direct the aldehyde:ketone ratio. However, where such directing groups are present on the target substrate, the methods produce product which maintain their high selectivity toward aldehydes, including those cases where this selectivity is even higher than when more traditional Wacker-type oxidation catalysts are used, under otherwise identical reactions conditions.

Such terminal olefin substrates may include those structures characterized as having a structure of Formula (1):

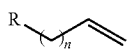

wherein:

n=0 to 24; and

R is H or a $C_{1-12}$-linear or branched alkyl optionally substituted with at least one of —$NH_2$, —$NH(C_{1-6}$-alkyl), —$N(C_{1-6}$-alkyl$)_2$, protected amine, amido, boronato, boryl, carbamoyl, cyano, cyanato, or halogen (including Br, Cl, F, and I), hydroxyl, protected hydroxyl, imino, nitro, nitroso, thiocyanato, isocyanate, thioisocyanate, epoxy, styrenyl, silanyl, silyl, silyloxy, siloxazanyl, optionally substituted $C_{1-12}$-alkyl, optionally substituted $C_{1-12}$-heteroalkyl, optionally substituted $C_{6-20}$-aryl, optionally substituted 5-20-membered-heteroaryl ring, optionally substituted $C_{2-30}$-alkaryl, optionally substituted $C_{7-30}$ aralkyl, optionally substituted —O—$C_{1-12}$-alkyl, optionally substituted —O—$C_{1-12}$-heteroalkyl, optionally substituted —O—$C_{6-20}$-aryl, optionally substituted —O—$C_{2-30}$-alkaryl, optionally substituted —O—$C_{2-30}$-aralkyl, optionally substituted —$C_1$-$C_{20}$ alkoxycarbonyl, optionally substituted $C_6$-$C_{20}$ aryloxycarbonyl, hydroxycarbonyl, carboxylato, mercapto, formyl, $C_1$-$C_{20}$ thioester, or where two substituents together with the methylene carbon form a $C_{3-6}$ cycloalkyl group; and, if substituted, the substituents may comprise at least one of $C_{1-12}$-alkyl, $C_{6-20}$-aryl, 5-20-membered-heteroaryl ring, phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amino, amido, imino, nitro, nitroso, hydroxyl, $C_1$-$C_{20}$ alkyl, $C_1$-$C_{20}$ alkoxy, $C_6$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen.

In some preferred embodiments, n is at least 2 when R=H.

Such a representation is intended to include those where n is 0, 1, 2, 3, 4, 5, 6, 7, 8, 9, 10, 11, 12, 13, 14, 15, 16, 17, 18, 19, 20, 21, 22, 23, 24, or any range having any of these numbers as endpoints—e.g., 0 to 6 or 6 to 12 or 4 to 18, etc. Note that when n is at least 2, the olefin may be characterized as "unbiased." Exemplary embodiments include optionally substituted 1-propene, 1-butene, 1-pentene, 1-hexene, 1-heptene, 1-octene, 1-nonene, 1-decene, 1-undecene, 1-dodecene, 1-tridecene, 1-tetradecene, 1-pentadecene, and so on, including linear and branched versions thereof, wherein the alkyl portion of the molecule is optionally functionalized with functional groups referred to herein as "Fn." For example, in some embodiments, R is H, optionally halogenated benzyl, cyclohexyl, or halogen. Structures such as shown in the Examples herein are also considered within the scope of this invention.

In some additional separate embodiments the substrates comprise chiral or achiral centers. Where described as including chiral centers, this includes mixtures containing racemic or enantiomeric mixtures, or mixtures of enriched amounts of such centers. As described below, in certain embodiments, the methods provide that the chirality of such substrate centers is maintained in the product aldehydes. See, e.g., Example 5.2.

In some embodiments, the substrate comprises at least one oxygen-bearing pendant group or a nitrogen-bearing pendant group in a position alpha (allylic) or beta (homoallylic) to the terminal olefin double bond. Non-limiting examples of an oxygen-bearing pendant group includes an optionally protected hydroxyl, —O—$C_{1-12}$-alkyl, optionally substituted —O—$C_{6-20}$-aryl, optionally substituted —O—$C_{5-20}$-heteroaryl, optionally substituted —O—$C_{7-30}$-aralkyl, optionally substituted —O—$C_{6-30}$-heteroaralkyl, optionally substituted —$C_1$-$C_{20}$ alkoxycarbonyl, or optionally substituted $C_6$-$C_{20}$ aryloxycarbonyl. In preferred embodiments, the at least one oxygen-bearing pendant comprises an optionally protected hydroxyl, $C_{1-6}$-alkoxy (preferably $C_{1-3}$-alkoxy), $C_{1-6}$-alkoxycarbonyl (preferably $C_{1-3}$-alkoxycarbonyl), acetoxy, benzyloxy, optionally substituted phenoxy, or optionally substituted benzyloxy. Certain representative oxygen-bearing functional groups are described in the Examples. Non-limiting examples of an nitrogen-bearing pendant group includes an optionally protected primary or secondary amines, for example—NHBoc, phthalimide, NH(benzyl), NH(tolylate), NH(phenyl), or tertiary amines or amides.

In addition to the methods described thus far, the invention also includes those reaction mixtures which effect the methods described. Without intending to limit the scope of this latter set of embodiments, an exemplary composition would include an aerobic mixture (or mixture derived from) of (a) a dichloro-palladium complex;

(b) a copper complex;

(c) a source of nitrite;

and optionally a terminal olefin.

Another exemplary composition would include an aerobic mixture of (a) bis(acetonitrile)dichloro-palladium(II) or bis(benzonitrile)dichloro-palladium(II);

(b) a copper source comprising $CuCl_2$, CuCl, or $CuCl_2 \cdot 2H_2O$;

(c) a nitrite source comprising $AgNO_2$ or $NaNO_2$;

dissolved or dispersed in a tert-butanol:nitromethane (15:1 vol/vol) solvent mixture;

under an air or oxygen atmosphere at a pressure of from about 1 to about 3 atmospheres at a temperatures in a range of from 15° C. to about 35° C., preferably 20° C. to about 25° C.;

an optionally a terminal olefin.

The present methods also allow for entry to a range of further reactions yielding additional functional groups. For example, a terminal olefin may be converted to a wide range of functional groups by first converting the terminal olefin to an aldehyde with high selectivity, using one or more of the embodiments described herein, and subsequently converting the aldehyde product, either in isolated form or as developed in situ, with other chemistries known to effect to the transformation of the aldehyde to such functional groups.

For example, certain embodiments provide methods for converting a terminal olefin to an acetal, acylal, terminal alcohol, α,β-unsaturated aldehyde, aldoxime, anhydride, amine, amide, carboxylic acid, carboxylate ester, epoxide, β-hydroxyester, α-hydroxy nitrile, hydrazone, nitrile, semicarbazone, halide, gem-dihalide, or α-halo ethers, said method comprising (a) converting the terminal olefin to a terminal aldehyde according to the methods described herein for doing so; and (b) converting the terminal aldehyde to a terminal alcohol, α,β-unsaturated aldehyde, carboxylic acid, carboxylate ester, amine, amide, or halide, step (b) being effected by known chemical methods. Such methods useful for effecting the aldehyde transformations include derivatization of or additions to aldehydes to form acetals, acylals, α,β-unsaturated carboxylic acid, 1,3 diols, epoxies, α,β-unsaturated epoxy ester, imides, aldoximes, α-amino nitrile, gem-dihalides, α-halo ethers, β-hydroxyesters, α-hydroxy nitriles, hydrazones, β-nitro alcohols, and semicarbazones; standard aldehyde reductions afford entries into alcohols, halides, amines, and amides; oxidation reactions to provide entries into carboxylic acids, carboxylate esters and amides. Such transformations are described in standard organic chemistry references such a Jerry March, ed., "Advanced Organic Chemistry, Reactions, Mechanisms, and Structure," McGraw-Hill, $2^{nd}$ Ed., 1977. Other transformation are described, for example, in Laszlo Kurti and Barbara Czako, "Strategic Applications of Named Reactions in Organic Synthesis", Academic Press, 2005, and include the aldol reaction, Barbier coupling reaction, Bayliss-Hillman reaction, Corey-Charkovsky epoxidation, Corey-Fuchs alkyne synthesis, Grignard reaction, Henry reaction, and HWE olefinations.

One non-limiting example of this strategy is shown in Example 5.2.

The following listing of embodiments in intended to complement, rather than displace or supersede, the previous descriptions.

Embodiment 1

A method of preparing organic aldehydes, said method comprising contacting a terminal olefin with an oxidizing mixture comprising (or resulting from the room temperature mixing of):

(a) a chloro- or dichloro-palladium complex;

(b) a copper complex;

(c) a source of nitrite;

under aerobic reaction conditions sufficient to convert at least a portion of the terminal olefin to an aldehyde. The source of nitrite may comprise a nitrite salt, an organic nitrite, or a nitrosonium salt, but should not be the palladium nitrite complex.

Embodiment 2

The method of Embodiment 1, wherein the source of nitrite is a salt of an alkali metal, alkaline earth metal, or silver.

Embodiment 3

The method of Embodiment 1 or 2, wherein the source of nitrite comprises $NaNO_2$ or $AgNO_2$.

Embodiment 4

The method of Embodiment 1, wherein the source of nitrite is $C_{1-6}$—ONO.

Embodiment 5

The method of any one of Embodiments 1 to 4, wherein the palladium complex comprises a dichloro-palladium complex optionally containing an organic nitrile ligand (e.g., acetonitrile or benzonitrile).

Embodiment 6

The method of any one of Embodiments 1 to 5, wherein the dichloro-palladium complex comprises bis(acetonitrile)dichloro-palladium(II) or bis(benzonitrile)dichloro-palladium(II).

Embodiment 7

The method of any one of Embodiments 1 to 6, wherein the copper complex is a copper halide, nitrate, nitrite, or tetrafluoroborate.

Embodiment 8

The method of any one of Embodiments 1 to 7, wherein the palladium and copper complexes act together as Wacker-type oxidation catalysts in the absence of the nitrite source, under otherwise identical reactions conditions.

Embodiment 9

The method of any one of Embodiments 1 to 8, wherein the mixture further comprises a non-nucleophilic or poorly nucleophilic solvent or solvent mixture.

Embodiment 10

The method of Embodiment 9, wherein the solvent or solvent mixture comprises tert-butanol (tert-BuOH).

Embodiment 11

The method of Embodiment 9 or 10, wherein the non-nucleophilic or poorly nucleophilic solvent or solvent mixture comprises tert-butanol (tert-BuOH) and nitromethane.

Embodiment 12

The method of any one of Embodiments 1 to 11, wherein the contacting of the terminal olefin and the oxidizing mixture is done in the presence of oxygen.

Embodiment 13

The method of any one of Embodiments 1 to 12, said method being catalytic with respect to the palladium.

Embodiment 14

The method of any one of Embodiments 1 to 13, wherein the olefin comprises a terminal olefin having a formula:

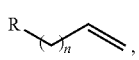

wherein:

n=0 to 24; and

R is H or a $C_{1-12}$-linear or branched alkyl optionally substituted with at least one of —$NH_2$, —$NH(C_{1-6}$-alkyl), —$N(C_{1-6}$-alkyl$)_2$, protected amine, amido, boronato, boryl, carbamoyl, cyano, cyanato, or halogen (including Br, Cl, F, and I), hydroxyl, protected hydroxyl, imino, nitro, nitroso, thiocyanato, isocyanate, thioisocyanate, epoxy, styrenyl, silanyl, silyl, silyloxy, siloxazanyl, optionally substituted $C_{1-12}$-alkyl, optionally substituted $C_{1-12}$-heteroalkyl, optionally substituted $C_{6-20}$-aryl, optionally substituted 5-20-membered-heteroaryl ring, optionally substituted $C_{7-30}$-alkaryl, optionally substituted $C_{7-30}$ aralkyl, optionally substituted —O—$C_{1-12}$-alkyl, optionally substituted —O—$C_{1-12}$-heteroalkyl, optionally substituted —O—$C_{6-20}$-aryl, optionally substituted —O—$C_{7-30}$-alkaryl, optionally substituted —O—$C_{7-30}$-aralkyl, optionally substituted —$C_1$-$C_{20}$ alkoxycarbonyl, optionally substituted $C_6$-$C_{20}$ aryloxycarbonyl, hydroxycarbonyl, carboxylato, mercapto, formyl, $C_1$-$C_{20}$ thioester, or where two substituents together with the methylene carbon form a $C_{3-6}$ cycloalkyl group; and, if substituted, the substituents may comprise at least one of $C_{1-12}$-alkyl, $C_{6-20}$-aryl, 5-20-membered-heteroaryl ring, phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amino, amido, imino, nitro, nitroso, hydroxyl, $C_1$-$C_{20}$ alkyl, $C_1$-$C_{20}$ alkoxy, $C_6$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen. In some preferred embodiments, n is at least 2 when R=H.

Embodiment 15

The method of Embodiment 14, wherein R is H, optionally halogenated benzyl, cyclohexyl, or halogen

Embodiment 16

The method of any one of Embodiments 1 to 15, wherein at least one of the substituents alpha (allylic) or beta (homoallylic) to the terminal olefin double bond is an optionally protected hydroxyl, —O—$C_{1-12}$-alkyl, optionally substituted —O—$C_{6-20}$-aryl, optionally substituted —O—$C_{5-20}$-heteroaryl, optionally substituted —O—$C_{2-30}$-aralkyl, optionally substituted —O—$C_{6-30}$-heteroaralkyl, optionally substituted —$C_1$-$C_{20}$ alkoxycarbonyl, or optionally substituted $C_6$-$C_{20}$ aryloxycarbonyl.

Embodiment 17

The method of any one of Embodiments 1 to 16, wherein at least one of the substituents alpha (allylic) or beta (homoallylic) to the terminal olefin double bond is an optionally protected hydroxyl, $C_{1-6}$-alkoxy, $C_{1-6}$-alkoxycarbonyl, acetoxy, benzyloxy, optionally substituted phenoxy, or optionally substituted benzyloxy.

Embodiment 18

A method of converting a terminal olefin to an acetal, acylal, terminal alcohol, α,β-unsaturated aldehyde, aldoxime, anhydride, amide, amine, α-amino nitrile, carboxylic acid, carboxylate ester, α,β-unsaturated carboxylic acid, 1,3 diol, epoxide, α,β-unsaturated epoxy ester, β-hydroxyester, α-hydroxy nitrile, hydrazone, nitrile, β-nitro alcohol, semicarbazone, halide, gem-dihalide, or α-halo ether, said method comprising (a) converting the terminal olefin to a terminal aldehyde according to any one of Embodiments 1 to 17; and (b) converting the terminal aldehyde to the acetal, acylal, terminal alcohol, α,β-unsaturated aldehyde, aldoxime, anhydride, amide, amine, α-amino nitrile, carboxylic acid, carboxylate ester, α,β-unsaturated carboxylic acid, 1,3 diol, epoxide, α,β-unsaturated epoxy ester, β-hydroxyester, α-hydroxy nitrile, hydrazone, nitrile, β-nitro alcohol, semicarbazone, halide, gem-dihalide, or α-halo ether.

EXAMPLES

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric.

Example 1

Introduction

During the course of their studies, the present inventors discovered that a variation of traditional Wacker-type oxidations could be used convert terminal olefins into aldehydes with remarkable yields and selectivies. At various points in the following discussion, this variation may be referenced as "the/an inventive method," or "nitrite-modified Wacker method." One of the attractive features of the present invention(s) is that the direct catalytic synthesis of aldehydes from terminal alkenes may therefore be regarded as a general entry into anti-Markovnikov functionalization. Prior to the present invention, this catalytic oxidation of unbiased alkenes to produce aldehydes remained elusive. General and efficient catalytic transformations have been developed to readily transform aldehydes into amines, alcohols and acids without generating wasteful byproducts. Furthermore, modern catalytic methodology has enabled powerful enantioselective carbon-carbon bond forming reactions from key aldehyde intermediates.

Figure 1A:
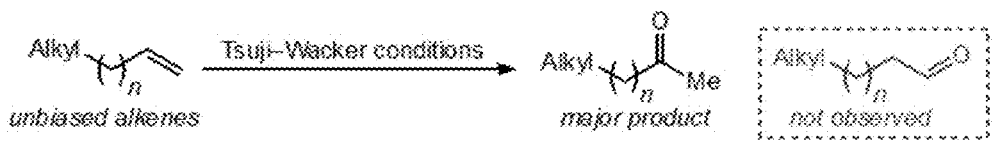
FIG. 1A shows classical Wacker oxidation of unbiased alkenes.

The Wacker oxidation (also referred to as the Tsuji-Wacker oxidation or reaction) is known for its ability to catalytically oxidize alkenes to carbonyls with high efficiency, high functional-group tolerance and minimal generation of waste. It has been studied for over half a century and has been broadly applied in both industrial and academic settings to synthesize methyl ketones from terminal alkenes. However, traditional Wacker oxidations are substrate-controlled and their regioselectivity is governed by Markovnikov's rule. Unbiased substrates such as aliphatic alkenes produce, at most, mere traces of anti-Markovnikov oxidation products under standard Tsuji-Wacker conditions (FIG. 1A). Attempts to produce aldehydes from unbiased alkenes (except ethylene) using Wacker oxidations have universally resulted in both low yield and poor selectivity.

Figure 1B:
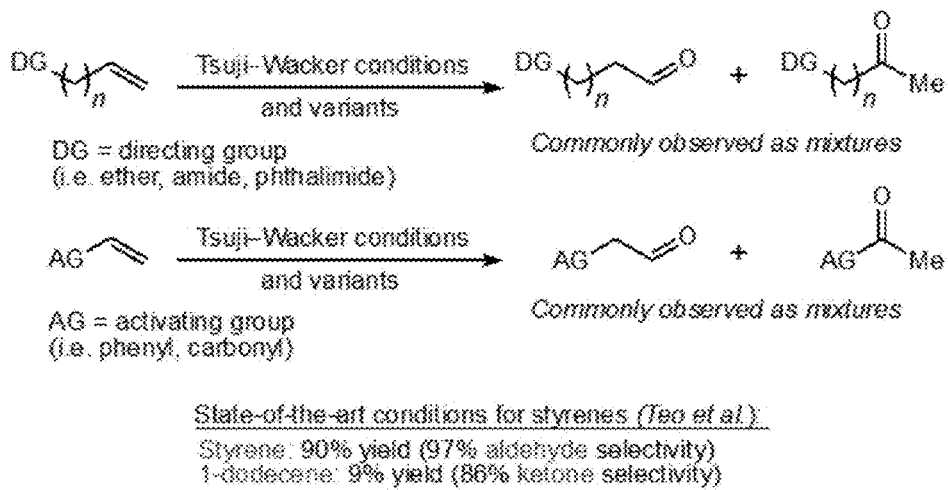
FIG. 1B shows common substrate-controlled strategies for aldehyde-selective Wacker.

Some researchers have attempted to exploit biased alkenes (bearing either a directing or activating group) to enable substrate-controlled anti-Markovnikov Wacker-type oxidation (FIG. 1B). Yet, even in these substrate-controlled cases, mixtures of aldehydes and ketones are typically observed, and only a few examples have provided useful yields and aldehyde-selectivities. The scope and utility of this approach is inherently limited because the vast majority of alkenes in feedstock and fine chemicals are unbiased and thus will adhere to Markovnikov's rule.

Figure 1C:
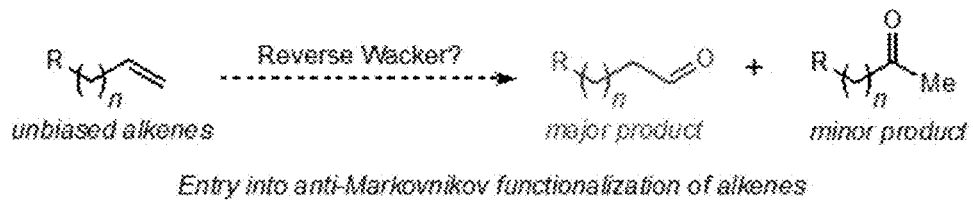
FIG. 1C shows a hypothetical aldehyde-selective Wacker oxidation.

The present invention, then, is striking in its surprising ability to provide a generally applicable aldehyde-selective Wacker oxidation that reverses the innate Markovnikov selectivity (FIG. 1C and FIG. 8).

Example 2

Materials and Methods $PdCl_2(PhCN)_2$, $CuCl_2.2H_2O$, $AgNO_2$, anhydrous tert-BuOH and $MeNO_2$ were obtained from Sigma-Aldrich and were used as provided. All other materials were either obtained from commercial sources or prepared using literature methods. $^1H$ and $^{13}C$ NMR spectra were recorded on a Varian 500 MHz, Varian 400 MHz or a Varian 300 MHz spectrometer. High-resolution mass spectra were provided by the California Institute of Technology Mass Spectrometry Facility using JEOL JMS-600H High Resolution Mass Spectrometer. GC-MS data was provided through the California Institute of Technology Mass Spectrometry Facility using HP 5970 series MSD with HP 5890 GC. Gas chromatography data was obtained using an Agilent 6850 FID gas chromatograph equipped with a HP-5 (5%-phenyl)-methylpolysiloxane capillary column (Agilent). Response factors relative to tridecane were collected for 1-dodecene, dodecanal and 2-dodecanone following literature procedures. See, T. Ritter, et al., *Organometallics* 25, 5740-5745 (2006).

Example 3

Oxidation of Unbiased Terminal Olefins

Figure 2A:
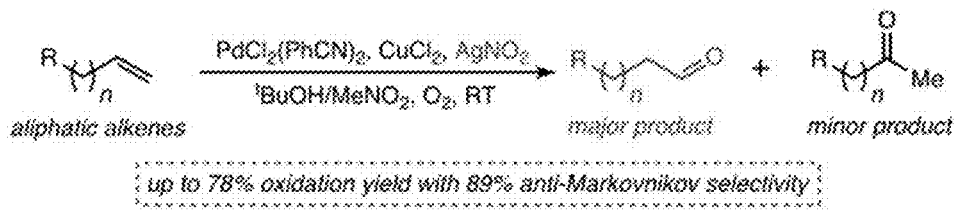
FIG. 2A shows a potential strategy to reverse the Markovnikov regioselectivity exhibited by the Wacker oxidation.
Figure 2B:
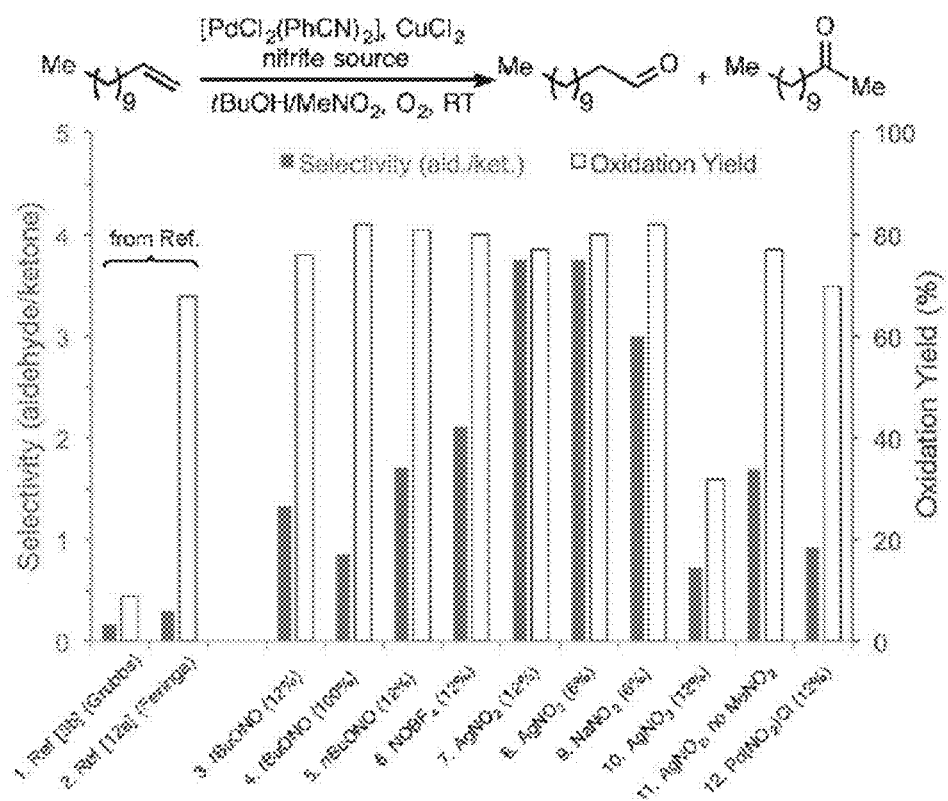
FIG. 2B shows various catalyst optimization data. For Entries 3-12: 1-dodecene (0.2 mmol), [$PdCl_2(PhCN)_2$] (12 mol %), and CuCl$_2$.2H2O (12 mol %) were used. For Entry 12: [PdCl$_2$(PhCN)$_2$] was replaced by [PdNO$_2$Cl(MeCN)$_2$].

Initial screening efforts used 1-dodecene as the model alkene. This unbiased substrate offered an excellent platform for the development of a catalyst-controlled process, since it contains no chemical handle to reverse the Markovnikov selectivity (FIG. 2A).

Example 3.1

General Procedures

Example 3.1.1

Procedure (A) for Larger-Scale (0.5 Mmol) Oxidation of Aliphatic Alkenes (Isolation)

$PdCl_2(PhCN)_2$ (0.06 mmol, 0.023 g), $CuCl_2*2H_2O$ (0.06 mmol, 0.0102 g) and $AgNO_2$ (0.03 mmol, 0.0046 g) were weighed into a 20 mL vial charged with a stir bar. The vial was sparged for 2 minutes with oxygen (1 atm, balloon). Premixed and oxygen saturated tert-BuOH (7.5 mL) and $MeNO_2$ (0.5 mL) was added followed by the alkene (0.5 mmol) were added in that order via syringe. The solution was saturated with oxygen by an additional 45 seconds of sparging. The reaction was then allowed to stir at room temperature for 6 hours. Next, the reaction was quenched by addition to water (ca. 50 mL) and extracted three times with dichloromethane (ca. 25 mL). The combined organic layers were subsequently washed with a saturated solution of $NaHCO_3$ and dried over $Na_2SO_4$. The solvent was removed under reduced pressure and the desired aldehyde product was purified using flash chromatography (pentane/ether). Selectivity was determined from $^1H$ NMR analysis of the unpurified mixture by ratio of the aldehydic $^1H$ signal to the most clear signal from the methyl ketone (usually the methyl group). Long relaxation delays (d1=15) were applied due to the long $T_1$ of the aldehydic proton signal.

Example 3.1.2

Procedure (B) for Smaller-Scale (0.2 Mmol) Oxidation of 1-Dodecene (GC Analysis)

$PdCl_2(PhCN)_2$ (0.024 mmol, 0.0092 g), $CuCl_2*2H_2O$ (0.024 mmol, 0.0041 g) and $AgNO_2$ (0.012 mmol, 0.0018 g) were weighed into a 2 dram screw-cap vial charged with a stir bar. The vial was sparged for 45 seconds with oxygen (1 atm, balloon) then subsequently tridecane (0.00246 mmol, 6 µL), tert-BuOH (3 mL), $MeNO_2$ (0.2 mL) and 1-dodecene (0.2 mmol, 44.4 µL) were added in that order via syringe. The solution was saturated with oxygen by an additional 45 seconds of sparging. The reaction was then allowed to stir at room temperature for 6 hours. Next, an aliquot (ca. 0.2 mL) was injected into a 2 mL vial containing an estimated 1 mL of premixed EtOAc/pyridine solution (3:1) to quench the reaction. The resulting solution was subsequently subjected to GC analysis to determine yield and selectivity.

Example 3.1.3

Procedure (C) for Small-Scale (0.2 Mmol) Oxidation of Alkenes (NMR Analysis)

$PdCl_2(PhCN)_2$ (0.024 mmol, 0.0092 g), $CuCl_2.2H_2O$ (0.024 mmol, 0.0041 g) and $AgNO_2$ (0.012 mmol, 0.0018 g) were weighed into a 2 dram screw-cap vial charged with a stir bar. The vial was sparged for 45 seconds with oxygen (1 atm, balloon) then subsequently tert-BuOH (3 mL), $MeNO_2$ (0.2 mL) and alkene (0.2 mmol) were added in that order via syringe. The solution was saturated with oxygen by an additional 45 seconds of sparging. The reaction was then allowed to stir at room temperature for 6 hours. Next, the reaction mixture was diluted with water (ca. 20 mL) and subsequently extracted three times with $CDCl_3$, dried with $Na_2SO_4$ and concentrated under reduced pressure for $^1H$ NMR analysis. Immediately prior to NMR analysis nitrobenzene was added as an internal standard. The resulting solution was subsequently subjected to $^1H$ NMR analysis to determine yield and selectivity by ratio of the aldehydic $^1H$ signal to the most clear signal from the methyl ketone (usually the methyl group). Long relaxation delays (d1=15) were applied due to the long t1 of the aldehydic proton signal.

Example 3.1.4

Procedure (D) for Stoichiometric Oxidation of 1-Dodecene (GC Analysis)

$PdCl_2(PhCN)_2$ (0.024 mmol, 0.0092 g), $CuCl_2.2H_2O$ (0.024 mmol, 0.0041 g) and $AgNO_2$ (0.012 mmol, 0.0018 g) were weighed into a 2 dram screw-cap vial charged with a stir bar. The vial was sparged for 45 seconds with oxygen (1 atm, balloon) then subsequently tridecane (0.00246 mmol, 6 µL), tert-BuOH (3 mL), MeNO$_2$ (0.2 mL) and 1-dodecene (0.024 mmol, 5.3 µL) were added in that order via syringe. The solution was saturated with oxygen by an additional 45 seconds of sparging. The reaction was then allowed to stir at room temperature for 3 hours and 30 minutes. Next, an aliquot (ca. 0.2 mL) was injected into a 2 mL vial containing an estimated 1 mL of premixed EtOAc/pyridine solution (3:1) to quench the reaction. The resulting solution was subsequently subjected to GC analysis to determine yield and selectivity.

Example 3.1.5

Procedures for Variation of Oxygen Atmosphere

A series of experiments to determine the effect of oxygen atmosphere were conducted, the results being shown in the following Table 1: Based on these data, and without being necessarily bound by the correctness of any particular theory or statement, it appeared that oxygen was the terminal oxidant and sole stoichiometric reagent in this system. Although reaction sealed under air resulted in acceptable yield (60%, see Table 1), the rate and conversion improved significantly under an oxygen atmosphere. Further increase in oxygen pressure (3 atm) did not provide increased efficiency but did marginally increase the selectivity.

TABLE 1

Oxygen atmosphere variation

| entry | Conditions | Overall yield (aldehyde yield) | selectivity |
|---|---|---|---|
| 1 | no O$_2$ (argon) | 12 (10) | 80% |
| 2 | air (sealed) | 60 (48) | 79% |
| 3 | air (open) | 38 (27) | 71% |
| 4 | O$_2$ (1 atm) | 80 (63) | 79% |
| 5 | O$_2$ (3 atm) | 68 (58) | 84% |

Entry 1: Conducted as described in procedure B except using a balloon filled with argon (1 atm) in place of a balloon filled with oxygen.
Entry 2: Conducted as described in procedure B except the reaction was never exposed to pure molecular oxygen.
Entry 3: Conducted as described in procedure B except the reaction was never exposed to pure molecular oxygen and the vial was left uncapped.
Entry 4: Conducted as described in procedure B with no deviation.
Entry 5: Conducted in an open vial placed inside a Fischer porter bottle connected to an oxygen tank and adjusted to 3 atm O$_2$.

Example 3.1.6

$^{18}$O-Labeling Studies (FIG. 4)

In a drybox under a nitrogen atmosphere, 1 mg (0.013 mmol) of isotopically labeled sodium nitrite, Na$^{15}$N$^{18}$O$_2$ (90% $^{18}$O, 95% $^{15}$N specified by Sigma-Aldrich) was weighed into a 2 mL vial, followed by the addition of 5.2 mg PdCl$_2$(PhCN)$_2$ (0.013 mmol) and 1.8 mg anhydrous CuCl$_2$ (0.013 mmol). 200 microliters of pre-mixed dry tert-BuOH and MeNO$_2$ (15:1) was then added, followed by vigorous agitation for one minute. Following agitation, 2 microliters (0.013 mmol) 4-phenyl-1-butene was added. The reaction mixture was stirred for 12 min at room temperature. An aliquot of the mixture 100 µL was then rapidly taken out of the drybox and quenched by addition into 1 mL dry pyridine, immediately followed by freezing in liquid nitrogen. The sample was kept at −178° C. and was allowed to warm to room temperature directly before injection into the GC-MS.

The level of incorporation was determined by the counts of m/z 150, 151 divided by the total counts (of m/z 148, 149, 150, 151). This % incorporation (73%) was then subsequently adjusted by the initial purity of the $^{18}$O-label (90%) to determine the percentage of $^{18}$O transferred from the nitrite salt (81%). The mass spectrum of $^{18}$O-enriched 4-phenylbutanal are provided in FIG. 5A.

Example 3.1.6.1

Control Experiment

The product aldehyde (4-phenylbutanal) was subjected to the same reaction conditions and subsequent analysis as described above for the labeling experiment. The % $^{18}$O transfer was thus determined to be 18%.

The reaction was not allowed to reach completion because residual water can rapidly exchange with the aldehyde signal by formation of a transient hemiacetal. This exchange would be expected to dilute the isotopic label. Thus, we suspect the 19% dilution of isotopic label can be accounted for by exchange of the aldehydic oxygen atom. The reaction yield was estimated by $^1$H NMR analysis (using benzonitrile as an internal standard) on an unlabeled sample prepared by the same protocol. Yield of aldehyde was estimated to be 36% from this analogous reaction. Labeling was also observed (to a lesser extent ~60%) in the ketone product. However, it has been previously shown with $^{18}$O-labeled nitrite that palladium can transfer oxygen from nitrite in a ketone selective Wacker-type oxidation. 4-Phenylbutene was selected as the substrate for its prominent molecular ion. The mass spectrum of 4-phenylbutanal subjected to the $^{18}$O-labeling conditions (control) is provided in FIG. 5B.

Example 3.1.6.2

In these labeling studies, the $^{18}$O-label was found to be effectively transferred from the labeled nitrite into the products, establishing the origin of the oxygen in the aldehyde. Stoichiometric oxygen transfer is expected to result in NO formation. Conceivably, under these catalytic reaction conditions, NO could be aerobically oxidized back to NO$_2$, enabling the catalytic use of the nitrite salt.

Example 3.2

Effect of Reaction Parameters (FIG. 3A)

Various redox catalysts, ligands, redox catalysts, palladium sources and a wide variety of additives were investigated. Each of the type of palladium and copper complexes, and the types of oxygen-centered radical species were found to play an important role in the overall performance of the catalytic system, as did the choice of solvent. Removal of any of these components results in dramatically poorer conversion, selectivity, or both.

In one variation of Procedure D, experiments were conducted with the omission of either copper or palladium. The GC was monitored over 3 hours and 30 minutes. When palladium was omitted: no conversion was observed. When copper was omitted: 33% yield (combined aldehyde and ketone) was observed with 53% ketone-selectivity. As a reference point, the analogous reaction with DMF/water and no AgNO$_2$ has proceeded to complete conversion with complete ketone selectivity within this time. The results are shown in FIG. 3B.

Removal of copper from the process provided only traces of products. Exposure of alkene to stoichiometric palladium and silver nitrite, however, also provided incomplete oxidation and poor selectivity, suggesting a more intimate role of the copper salt than a simple redox catalyst for palladium (FIG. 3B). Furthermore, stoichiometric copper dichloride and silver nitrite (no palladium) provided no conversion of the alkene. Thus, it appears that both palladium and copper are crucial metals for the efficient stoichiometric oxidation of alkenes. Ag(I) salts have been shown to be non-innocent additives (potential oxidants) in palladium-catalyzed reactions. However, if AgNO$_2$ was replaced by NaNO$_2$, a similar reaction outcome was observed with marginally lower selectivity (FIG. 3C). This strongly implied that nitrite was the critical component of the co-catalyst, not Ag(I).

Detailed reaction profiles employing various quantities of AgNO$_2$ (FIG. 3D) were generated to study the effect of time on the reaction. Increased loading of AgNO$_2$ correlated with a faster reaction, implying a rate dependence on AgNO$_2$ concentration. A similar overall yield of aldehyde was obtained using both 12 and 6 mol % AgNO$_2$, with slightly improved aldehyde yield using 6 mol %. Interestingly, even 2 mol % AgNO$_2$ provided useful yields of aldehyde after a longer reaction time. Omission of AgNO$_2$ led to a process not exceeding 20% overall yield.

In a related series of experiments, Procedure B was used to measure the progress of the reaction with time. Time points were collected with a Freeslate (formerly Symyx) software system at the given times and quenched with a 3:1 mixture of EtOAc and pyridine, followed by GC analysis using tridecane as an internal standard. Reaction temperature is further maintained at 20° C. throughout the course of the reaction. Variation of nitrite loading was accomplished with no further deviation from protocol B. After GC analysis, the data was processed and graphed using Microsoft Excel. See again FIG. 3D.

In contrast to previous attempts by others to develop and aldehyde-selective Wacker-type oxidation, that have been plagued by low yields and loss of selectivity over the course of the reaction, in the present experiments, tests with 1-dodecene showed the selectivity stabilized after 5% conversion and became relatively independent of both yield and time. See FIG. 3E.

Other nitrite sources, including organic and inorganic derivatives, were evaluated by Procedure B. Catalytic AgNO$_2$ was found to provide the highest selectivity among nitrite sources (see Table 2).

TABLE 2

Nitrite sources (obtained by procedure B)

| entry | Conditions | Overall yield (aldehyde yield) | selectivity |
|---|---|---|---|
| 1 | tert-BuONO | 75 (41) | 55% |
| 2 | n-BuONO | 76 (34) | 45% |
| 3 | NOBF$_4$ | 73 (42) | 59% |
| 4 | Pd(NO$_2$)Cl(MeCN)$_2$ | 80 (21) | 29% |
| 5 | AgNO$_2$ | 80 (63) | 79% |
| 6 | NaNO$_2$ | 82 (61) | 75% |

From these studies, co-catalytic nitrite salts were found to provide unparalleled reactivity in the presence of palladium and copper. Intriguingly, when the reaction was conducted in an open vessel, both yield and selectivity were significantly worse than when sealed under air. (see Table 1).

The introduction of a small amount of a polar co-solvent, nitromethane, both increased homogeneity of the reaction mixture and enabled room temperature reaction. Once optimized, the new conditions (PdCl$_2$(PhCN)$_2$ (12 mol %), CuCl$_2$*2H$_2$O (12 mol %), AgNO$_2$ (6 mol %) in tert-BuOH/MeNO$_2$ (15:1) under 1 atm oxygen) oxidized 1-dodecene to dodecanal in 63% yield (see also FIG. 2A/2B and FIG. 3A).

Example 3.3

Effect of Substrate on Catalytic System

Having developed oxidation conditions capable of providing synthetically useful yields and aldehyde-selectivities, experiments were done to explore the functional group tolerance of the transformation (Table 3). To avoid substrate-controlled anti-Markovnikov selectivity, aliphatic substrates bearing only distal functionality were selected. These substrates provided yields comparable to those expected under Tsuji-Wacker conditions, but with anti-Markovnikov selectivity. The reaction was compatible with a diverse array of functional groups: alkyl and aryl halides, carboxylic acids, esters, alcohols, ethers, and nitro groups were all tolerated. Despite the potential challenge of using unprotected functional groups, carboxylic acids and alcohols still provided synthetically viable yields of the corresponding aldehyde products. Importantly, although alkene isomerization is a common problem in Wacker-type oxidations, no significant isomerization was observed with any of the substrates, even in potentially challenging substrates such as 4-phenylbutene.

TABLE 3

Aldehyde-selective Wacker-type oxidation of unbiased alkenes[a]

$$R\diagup\diagdown \xrightarrow[\text{\textsuperscript{t}BuOH/MeNO}_2 \text{ (15:1), RT, O}_2 \text{ (1atm)}]{\text{PdCl}_2(\text{PhCN})_2 \text{ (12\%), CuCl}_2 \text{ (12\%),} \text{ AgNO}_2 \text{ (6\%)}} R\diagup\diagdown\diagup^{\text{O}} + R\diagup\diagdown\diagup\text{(=O)Me}$$

| Entry | Substrate | Overall yield[b] (aldehyde yield) | Selectivity[c] |
|---|---|---|---|
| 1 | ⩘($)_8$Me | 80 (63)[d] | 79% |
| 2 |  | 74 (61) | 79% |
| 3 | ⩘($)_2$NO$_2$ | 78 (70) | 89% |
| 4 | ⩘($)_7$CO$_2$Me | 80 (63) | 79% |
| 5 | ⩘($)_2$CO$_2$H | 68 (51)[e] | 67% |
| 6 | ⩘($)_5$Br | 77 (65) | 82% |
| 7 | ⩘($)_6$OBn | 70 (59) | 81% |

TABLE 3-continued

Aldehyde-selective Wacker-type oxidation of unbiased alkenes[a]

R⟶ [PdCl₂(PhCN)₂ (12%), CuCl₂ (12%), AgNO₂ (6%), tBuOH/MeNO₂ (15:1), RT, O₂ (1 atm)] ⟶ R-CH₂-CHO + R-C(O)-Me

| Entry | Substrate | Overall yield[b] (aldehyde yield) | Selectivity[c] |
|---|---|---|---|
| 8 | CH₂=CH-(CH₂)₆-OH | 80 (45) | 57% |
| 9 | CH₂=CH-CH₂-Cy | 75 (60)[f] | 80% |
| 10 | CH₂=CH-CH₂-CH₂-Ph | 75 (68) | 89% |
| 11 | CH₂=CH-CH₂-CH₂-(2-Br-C₆H₄) | 71 (64)[f] | 90% |

[a]0.5 mmol alkene treated with PdCl₂(PhCN)₂ (12 mol %), CuCl₂*2H₂O (12 mol %), AgNO₂ (6 mol %), tBuOH/MeNO₂ (15:1) under O₂ (1 atm) at room temperature (20-25° C.).
[b]Yield of aldehyde was determined by isolation (0.5 mmol scale) and overall yield was calculated using the aldehyde-selectivity.
[c]Selectivity calculated by ¹H-NMR analysis of the unpurified reaction mixture.
[d]Yield and selectivity both obtained by gas chromatography analysis using tridecane as an internal standard.
[e]Yield determined via 1H-NMR analysis using mesitylene as an internal standard.
[f]Yield determined via 1H-NMR analysis using nitrobenzene as an internal standard and scale was adjusted to 0.2 mmol alkene.

Example 3.4

Scalability

In assessing the scalability of the process, the catalysts loadings were reduced to 7 mol % to accommodate a gram-scale process (Scheme 1). The success of this large-scale reaction demonstrated that the process can maintain high yield and aldehyde selectivity at an increased scale, even with decreased catalyst loading.

Scheme 1. Aldehyde-selective Wacker oxidation on a 10 mmol scale with reduced catalyst loading

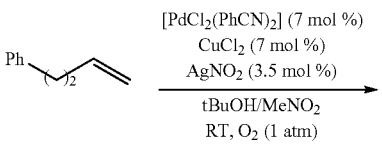

[PdCl₂(PhCN)₂] (7 mol %)
CuCl₂ (7 mol %)
AgNO₂ (3.5 mol %)
tBuOH/MeNO₂
RT, O₂ (1 atm)

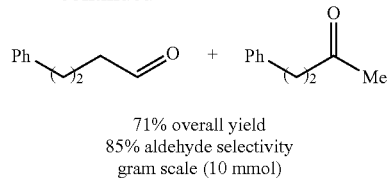

71% overall yield
85% aldehyde selectivity
gram scale (10 mmol)

Example 3.5

Characterizations of Products in Table 3

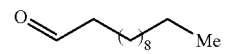

Dodecanal (Table 1, Entry 1)

63% aldehyde yield obtained using procedure B.

Dodecanal (Table 1, Entry 2)

61% yield obtained using procedure A. ¹H NMR (500 MHz, CDCl₃) δ 9.76 (t, J=1.9 Hz, 1H), 2.43 (td, J=7.4, 1.9 Hz, 2H), 1.64 (tt, J=7.5, 7.5 Hz, 2H), 1.49-1.18 (m, 16H), 0.97-0.77 (t, J=6.8, 3H). Spectral data were in accordance with a commercial sample.

5-Nitropentanal (Table 1, Entry 3)

70% obtained using procedure A. ¹H NMR (400 MHz, CDCl₃) δ 9.78 (t, J=1.1 Hz, 1H), 4.40 (t, J=6.8 Hz, 2H), 2.54 (td, J=7.1, 1.1 Hz, 2H), 2.09-2.00 (m, 2H), 1.77-1.68 (m, 2H). ¹³C NMR (101 MHz, CDCl₃) δ 200.84, 75.17, 42.78, 26.57, 18.74. HRMS (EI⁺) calcd for C₄H₈O₂N (M-CHO) 102.0555. found 102.0560.

Methyl 11-oxoundecanoate (Table 1, Entry 4)

63% yield obtained using procedure A. ¹H NMR (500 MHz, CDCl₃) δ 9.74 (t, J=1.9 Hz, 1H), 3.56 (s, 3H), 2.40 (td, J=7.4, 1.9 Hz, 2H), 2.28 (t, J=7.6 Hz, 2H), 1.73-1.48 (m, 4H), 1.34-1.20 (s, 10H). Spectral data were in accordance with the literature (49).

7-Oxoheptanoic Acid (Table 1, Entry 5)

51% aldehyde yield obtained using procedure C with the following modifications: work up was conducted by initial dilution with 0.5M HCl instead of water and mestiylene was added as an internal standard instead of nitrobenzene.

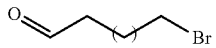

8-Bromooctanal (Table 1, Entry 6)

65% yield obtained using procedure A. $^1$H NMR (300 MHz, CDCl$_3$) 9.76 (t, J=1.8 Hz, 1H), 3.40 (t, J=6.8 Hz, 2H), 2.42 (td, J=7.3, 1.8 Hz, 2H), 1.83 (p, J=6.8 Hz, 2H), 1.62 (m, 2H), 1.42 (m, 2H), 1.34 (m, J=5.1, 3.7 Hz, 4H). Spectral data were in accordance with the literature (50).

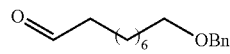

9-(Benzyloxy)Nonanal (Table 1, Entry 7)

59% yield obtained using procedure A. $^1$H NMR (300 MHz, CDCl$_3$) δ 9.76 (t, J=1.9 Hz, 1H), 7.39-7.27 (m, 5H), 4.50 (s, 2H), 3.46 (t, J=6.6 Hz, 2H), 2.53-2.31 (td, J=7.4, 1.9 Hz, 2H), 1.70-1.53 (m, 4H), 1.42-1.22 (m, 8H). Spectral data were in accordance with the literature (51).

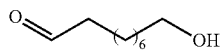

9-Hydroxynonanal (Table 1, Entry 8)

45% yield obtained using procedure A. $^1$H NMR (500 MHz, CDCl$_3$) δ 9.76 (t, J=1.8 Hz, 1H), 3.64 (t, J=5.6 Hz, 2H), 2.43 (td, J=7.4, 1.9 Hz, 2H), 1.69-1.24 (m, 12H). Spectral data were in accordance with the literature (52).

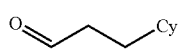

3-Cyclohexylpropanal (Table 1, Entry 9)

60% aldehyde yield obtained using procedure C.

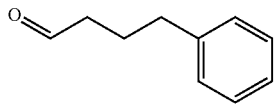 [SMILES: O=CCCCc1ccccc1]

4-Phenylbutanal (Table 1, Entry 10)

68% yield obtained using procedure A. $^1$H NMR (500 MHz, CDCl$_3$) δ 9.76 (t, J=1.6 Hz, 1H), 7.32-7.27 (m, 2H), 7.24-7.15 (m, 3H), 2.67 (t, J=7.6 Hz, 2H), 2.46 (td, J=7.3, 1.6 Hz, 2H), 1.97 (p, J=7.4 Hz, 2H). Spectral data were in accordance with the literature (53).

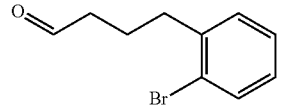 [SMILES: O=CCCCc1ccccc1Br]

4-(2-Bromophenyl)Butanal (Table 1, Entry 11)

64% aldehyde yield obtained using procedure C.

Example 4

Oxidation of Directed Olefins

Example 4.1

General Procedures

Example 4.2.1

Procedure a for Preparative Scale (0.5 Mmol) Oxidation of Alkenes (Isolation)

The preparative scale procedures used for directed olefins was the analogous to Procedure (A) used as for unbiased olefins, except for reduced catalysts loadings: PdCl$_2$(PhCN)$_2$ (0.05 mmol, 19.2 mg), CuCl$_2$.2H$_2$O (0.05 mmol, 8.5 mg) and NaNO$_2$ (0.025 mmol, 1.7 mg).

Example 4.2.2

Procedure B for Analytical Scale (0.2 Mmol) Oxidation of Alkenes (NMR Analysis)

The NMR analytical procedures used for directed olefins was the analogous to Procedure (C) used as for unbiased olefins, except for reduced catalysts loadings: PdCl$_2$(PhCN)$_2$ (0.02 mmol, 7.7 mg), CuCl$_2$.2H$_2$O (0.02 mmol, 3.6 mg) and NaNO$_2$ (0.01 mmol, 0.7 mg).

Example 4.2.3

Procedure for Tsuji-Wacker Oxidations

PdCl$_2$ (1.8 mg, 0.01 mmol) and CuCl (9.9 mg, 0.1 mmol) were weighed into an 8 mL vial. DMF (0.7 mL) and water (0.1 mL) were both added to the vial. The vial was sparged with oxygen (1 atm, balloon) for 3 minutes. The solution was stirred for another 1 h before alkene (0.1 mmol) was added. The reaction was stirred for at room temperature (20-25° C.). After 24 h, the reaction mixture was quenched by addition of water (ca. 10 mL) and extracted 3 times with dichloromethane (ca. 5 mL). The combined organic layers were subsequently washed with a saturated solution of LiCl(aq). After volatiles were removed under reduced pressure, nitrobenzene was added as an internal standard. The resulting solution was subsequently subjected to $^1$H NMR analysis to determine yield and selectivity.

Example 4.2.4

Intramolecular Competition Experiments

Each initial rate measurement was made in duplicate and the values averaged. The following procedure was used:

PdCl₂(PhCN)₂ (0.02 mmol, 7.7 mg), CuCl₂·2H₂O (0.02 mmol, 3.6 mg) and NaNO₂ (0.01 mmol, 0.7 mg) were weighed into a 8 mL vial charged with a stir bar. The vial was sparged for 1 minute with oxygen (1 atm, balloon). Premixed and oxygen saturated tert-BuOH (3 mL) and MeNO₂ (0.2 mL) was added followed by the addition of pre-mixed alkenes (0.1 mmol of each alkene). The solution was saturated with oxygen by an additional 10 seconds of sparging. The reaction was then allowed to stir at room temperature (20-25° C.) for 10 minutes. Next, the reaction was quenched by addition of pyridine (5 µL) and then water (10 mL) and extracted three times with dichloromethane (ca. 5 mL). The combined organic layers were subsequently washed with a saturated solution of NaHCO₃ (ca. 5 mL) and dried over Na₂SO₄. The resulting solution was subjected to ¹H NMR analysis to determine relative rates. Benzonitrile signals were used as an internal standard to confirm that conversion was <15% in each case. The selectivity of each substrate under the nitrite-modified Wacker was independently measured using procedure B.

Example 4.3

Results and Discussion

A series of alkene-containing phenyl ether substrates of varying chain length were subjected to both nitrite-modified Wacker conditions and Tsuji-Wacker conditions to evaluate the influence of proximal oxygen-containing functional groups on the regioselectivity (Table 4). The high anti-Markovnikov selectivity exhibited by an unbiased substrate (1-dodecene) under nitrite-modified Wacker conditions was markedly enhanced as the ether moiety approached the alkene (Table 4). Exceptional aldehyde selectivity (>90%) was observed with both the allylic (n=1) and homoallylic phenyl ether (n=2), despite the significant difference in the innate regioselectivity of the two substrates under Tsuji-Wacker conditions. Moreover, substrates bearing a distal ether functional group (n=3) retained the high regioselectivity observed in the unfunctionalized systems. These encouraging results were consistent with a catalyst-controlled process in which the selectivity was further enhanced by proximal heteroatoms. Consistent with earlier observations with unbiased aliphatic substrates (e.g., Example 2), both AgNO₂ and NaNO₂ were found to be effective sources of nitrite; however, with oxygenated alkenes, NaNO₂ proved to be more effective and inexpensive source of nitrite.

TABLE 4

Influence of phenoxy group proximity on regioselectivity in Wacker-type conditions.

| | Nitrite-Wacker (A) | Tsuji-Wacker (B) |
|---|---|---|
| n = 1 | 95% | 41% |
| n = 2 | 92% | ≤5% |
| n = 3 | 75% | ≤5% |
| n = 4 | 79% | ≤5% |

Conditions A: PdCl₂(PhCN)₂ (12 mol %), CuCl₂·H₂O (12 mol %), AgNO₂ (6 mol %), tert-BuOH/MeNO₂ (15:1), RT, O₂ (1 atm), 6 hrs.
Conditions B: PdCl₂ (10%), CuCl (1 equiv), DMF/H₂O (7:1), RT, O₂ (1 atm), 24 hr.

To be a general catalyst-controlled methodology to access functionalized aldehydes, the high anti-Markovnikov selectivity must not be dependent on specific directing groups. With this in mind, a collection of substrates bearing different oxygen-containing functional groups were examined in both the allylic or homoallylic position under the optimized conditions (Table 5). The oxidation of these substrates took place with high aldehyde selectivity (89-96%), allowing the aldehyde product to be isolated in prepartively useful yields (64-88%), irrespective of the nature of the oxygen-containing functional group. In particular, alkyl, aryl and silyl ethers, as well as acetyl esters, were all well tolerated. For comparison, each substrate was additionally subjected to Tsuji-Wacker conditions to determine its innate selectivity. In contrast to the high anti-Markovnikov selectivity observed across the series under nitrite-modified Wacker conditions, the innate selectivity varied greatly as a function of substrate. The excellent aldehyde selectivity provided by the nitrite-modified Wacker oxidation of homoallylic substrates is particularly notable due to their high innate Markovnikov selectivity (≥80% ketone selective). Notably, the selectivity was independent of the innate selectivity, clearly demonstrating catalyst-controlled regioselectivity.

TABLE 5

Influence of Steric Profile on Aldehyde-Selective Wacker[a]

| Entry | Substrate | Nitrate Source | Aldehyde Yield[b] | Selectivity | Innate Selectivity (Tsuji-Wacker)[d] |
|---|---|---|---|---|---|
| 1 | 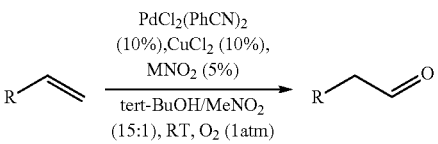 | NaNO₂ | 80% | 93:7 | 7:93 |

TABLE 5-continued

Influence of Steric Profile on Aldehyde-Selective Wacker[a]

R—CH=CH2 →[PdCl2(PhCN)2 (10%), CuCl2 (10%), MNO2 (5%), tert-BuOH/MeNO2 (15:1), RT, O2 (1atm)] R—CH2—CHO

| Entry | Substrate | Nitrate Source | Aldehyde Yield[b] | Selectivity | Innate Selectivity (Tsuji-Wacker)[d] |
|---|---|---|---|---|---|
| 2 | OBn, Ph (allyl) | NaNO2 | 74% | 94:6 | 20:80 |
| 3 | OBn, Me, n-Pr (allyl) | NaNO2 | 51%[e] | 93:7 | 9:91 |
| 4 | " | AgNO2 | 77%[f] | 90:10 | — |
| 5 | OBn, cyclohexyl (allyl) | NaNO2 | 37%[e] | 95:5 | 8:92 |
| 6[g] | " | NaNO2 | 75%[e] | 88:12 | — |
| 7[g] | " | AgNO2 | 77% | 95:5 | — |
| 8 | OBn, Me, Ph (allyl) | NaNO2 | 38%[e] | 66:34 | 10:90 |
| 9[g] | " | AgNO2 | 65% | 75:25 | — |

[a]0.5 mmol of alkene (0.0625 M), 5 h.
[b]Yield of isolated aldehyde product.
[c]Selectivity (aldehyde/ketone) obtained by ¹H NMR analysis of the unpurified reaction mixture.
[d]0.1 mmol of alkene, PdCl2 (10 mol %), CuCl (1 equiv), DMF/H2O (7:1, 0.125 M), rt (2.0-25° C.), run to ≤95% conversion (24 h). Selectivity determined by ¹H NMR analysis.
[e]Yield determined by ¹H NMR analysis.
[f]Isolated as an inseparable mixture of aldehyde and ketone
[g]24 h reaction time A series of experiments were conducted to explore the effects of the steric properties of this class of substrates influences reactivity and selectivity (Table 6). Having demonstrated that such substrates perform similarly in the reaction irrespective of the substituent on oxygen, a benzyl group was selected as a representative protecting group. Variation at the α-position of the ether provided no significant effect on yield or selectivity (Table 6, entries 1 and 2). Bulkier substrates required an increased reaction time and replacement of NaNO2 with the more active AgNO2 to provide an analogous yield and selectivity (entries 4-9). In order to assess the applicability of the process on a larger scale, the reaction was attempted on a 4-g scale with a reduced catalyst loading.

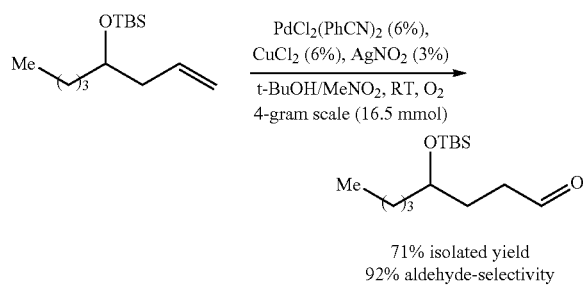

71% isolated yield
92% aldehyde-selectivity

The reaction was 92% aldehyde selective, delivering 71% of the aldehyde product.

The relative rates of functionalized and unfunctionalized substrates were studied in a series of one-pot intermolecular competition experiments (FIG. 6). Both functionalized substrates exhibited a substantial increase in the rate of aldehyde formation relative to the unfunctionalized 1-dodecene. Without being bound by the correctness of any particular theory, it is possible that coordination of the Lewis basic oxygen atom to palladium increased the rate since inductive effects would be mitigated as the oxygen atom is moved further from the alkene.

To probe the role of the oxygen atom, allylic and homoallylic aryl ethers of varied electronic profiles were prepared and evaluated under the reaction conditions. Inductive effects have recently been demonstrated to play a major role in determining regioselectivity in palladium catalyzed processes. Interestingly, under the nitrite-modified Wacker conditions, the aldehyde selectivity and rate are only subtly influenced by electronic variation (FIG. 7). The minimal inductive influence was consistent with an apolar, radical type addition. These experiments suggest that electronic modulation does little to enhance or mitigate the coordinating influence of the Lewis basic oxygen functional groups.

Example 4.4

Allylic and Homoallylic Phthalimides

A set of three phthalimides, which upon minor carbon skeletal changes range from aldehyde- to ketone-selective control under traditional substrate controlled Tsuji-Wacker conditions were subjected to the present reaction conditions (FIG. 8). For each substrate, aldehyde products were obtained with high yield and selectivity, regardless of the innate Wacker selectivity. These results illustrate the efficacy of the present process(es) with proximal nitrogen functionality without reliance upon the substrate-controlled regioselectivity.

Example 4.5

Characterization

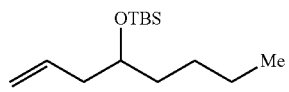 [SMILES: C=CCC(CCCC)O[Si](C)(C)C(C)(C)C]

tert-Butyldimethyl(oct-1-en-4-yloxy)silane

Prepared according to the literature. See *Org. Lett.* 2012, 14, 5728-5731. $^1$H NMR (500 MHz, CDCl$_3$) δ 5.87-5.74 (m, 1H), 5.07-5.02 (m, 1H), 5.02-4.99 (m, 1H), 3.68 (p, J=5.8 Hz, 1H), 2.29-2.14 (m, 2H), 1.50-1.21 (m, 6H). 0.89 (s, 9H), 0.88 (m, 3H), 0.05 (s, 6H). Spectral data were in accordance with the literature.

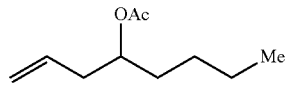

Oct-1-en-4-yl acetate

4-Dimethylaminopyridine (122 mg, 1 mmol) was weighed into a flask with a stir bar. Dichloromethane (10 mL), 1-octen-4-ol (1.54 mL, 10 mmol), acetic anhydride (1.9 mL, 20 mmol) was added to the vial and stirred overnight (10 hours). The reaction mixture was diluted with water (ca. 125 mL) and extracted with dichloromethane (ca. 50 mL×3) and the combined organics were washed with brine and subsequently dried over MgSO$_4$. Purification by column chromatography gave the desired compound (1.52 g, 89% yield) as a colorless oil. $^1$H NMR (500 MHz, CDCl$_3$) δ 5.73 (ddt, J=17.2, 10.2, 7.1 Hz, 1H), 5.08-5.00 (m, 2H), 4.89 (ddd, J=12.7, 6.6, 5.7 Hz, 1H), 2.34-2.22 (m, 2H), 2.01 (s, 3H), 1.59-1.47 (m, 2H), 1.45-1.17 (m, 4H), 0.96-0.81 (m, 3H). $^{13}$C NMR (126 MHz, CDCl$_3$) δ 170.71, 133.78, 117.47, 73.27, 38.62, 33.24, 27.43, 22.49, 21.17, 13.93. HRMS (EI$^+$) calc'd for C$_7$H$_{13}$O$_2$ (M-CH$_2$CHCH$_2$) 129.0916. found 129.0917.

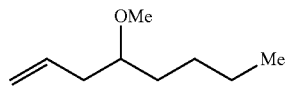

4-Methoxyoct-1-ene

NaH (60 wt % dispersion in mineral oil, 600 mg, 15 mmol) was weighed into a flask with a stir bar. Tetrahydrofuran (10 mL) was added to the vial and the mixture was cooled to 0° C. 1-Octen-4-ol (1.54 mL, 10 mmol) were added slowly to the suspension. MeI (0.75 mL, 12 mmol) was next added slowly to the reaction mixture. The reaction mixture was allowed to warm to room temperature and stirred overnight (ca. 10 h). The reaction mixture was diluted with water (ca. 125 mL) and extracted with diethyl ether (ca. 50 mL×3) and the combined organics were washed with brine and subsequently dried over MgSO$_4$. Purification by column chromatography gave the desired compound (1.01 g, 71% yield) as a colorless oil. $^1$H NMR (500 MHz, CDCl$_3$) δ 5.82 (ddt, J=17.2, 10.2, 7.1 Hz, 1H), 5.06 (m, 2H), 3.34 (s, 3H), 3.20 (p, J=5.9 Hz, 1H), 2.26 (m, 2H), 1.47 (m, 2H), 1.31 (m, 4H), 0.90 (m, 3H). Spectral data were in accordance with the literature. See *J. Org. Chem.* 2000, 65, 6254-6256.

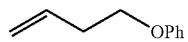

(but-3-en-1-yloxy)benzene

Prepared according to the literature. 3 $^1$H NMR (500 MHz, CDCl$_3$) δ 7.31-7.26 (m, 2H), 6.97-6.92 (m, 1H), 6.92-6.90 (m, 2H), 5.95 (ddt, J=17.1, 10.3, 6.7 Hz, 1H), 5.20-5.09 (m, 2H), 4.03 (t, J=6.7 Hz, 2H), 2.60-2.51 (m, 2H). Spectral data were in accordance with the literature. See *J. Org. Chem.* 2009, 74, 2854-2857.

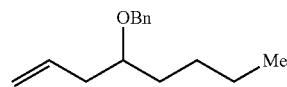 [SMILES: C=CCC(CCCC)OCc1ccccc1]

((oct-1-en-4-yloxy)methyl)benzene

NaH (60 wt % dispersion in mineral oil, 600 mg, 15 mmol) was weighed into a flask with a stir bar. Tetrahydrofuran (10 mL) was added to the vial and the mixture was cooled to 0° C. 1-Octen-4-ol (1.54 mL, 10 mmol) was added slowly to the suspension. Benzyl bromide (1.4 mL, 12 mmol) was next added slowly to the reaction mixture. The reaction mixture was allowed to warm to room temperature and stirred overnight (ca. 10 h). The reaction mixture was diluted with water (ca. 125 mL) and extracted with diethyl ether (ca. 50 mL×3) and the combined organics were washed with brine and subsequently dried over MgSO$_4$. Purification by column chromatography gave the desired compound (1.48 g, 68% yield) as a colorless oil. $^1$H NMR (500 MHz, CDCl$_3$) δ 7.41-7.34 (m, 4H), 7.33-7.27 (m, 1H), 5.89 (ddt, J=17.2, 10.2, 7.1 Hz, 1H), 5.21-5.06 (m, 2H), 4.60 (d, J=15.0 Hz, 1H), 4.52 (d, J=15.0 Hz, 1H), 3.47 (dq, J=6.7, 5.6 Hz, 1H), 2.47-2.26 (m, 2H), 1.67-1.50 (m, 2H), 1.50-1.26 (m, 4H), 0.93 (t, J=7.0 Hz, 1H). $^{13}$C NMR (126 MHz, CDCl$_3$) δ 138.97, 135.12, 128.29, 127.72, 127.42, 116.79, 78.58, 70.89, 38.33, 33.52, 27.58, 22.81, 14.11. HRMS (EI$^+$) calc'd for C$_{12}$H$_{17}$O (M-CH$_2$CHCH$_2$) 177.1279. found 177.1284.

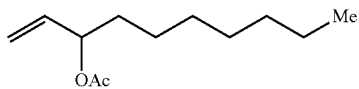

Dec-1-en-3-yl acetate prepared according to the literature. 4 ¹H NMR (500 MHz, CDCl₃) δ 5.82-5.72 (m, 1H), 5.26-5.19 (m, 2H), 5.14 (dt, J=10.4, 1.2 Hz, 1H), 2.05 (s, 3H), 1.72-1.52 (m, 2H), 1.36-1.23 (m, 10H), 0.90 (d, J=12.5 Hz, 3H). Spectral data were in accordance with the literature. *J. Organomet. Chem.* 2009, 694, 551-560.

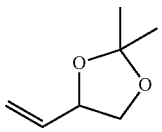

2,2-Dimethyl-4-vinyl-1,3-dioxolane prepared according to the literature. See *Tetrahedron: Asymmetry* 1996, 7, 3593. ¹H NMR (300 MHz, CDCl₃) δ 5.82 (m, 1H), 5.36 (m, 1H), 5.22 (ddd, J=10.3, 1.5, 0.8 Hz, 1H), 4.50 (dtd, J=7.3, 6.7, 6.3, 0.9 Hz, 1H), 4.11 (dd, J=8.1, 6.2 Hz, 1H), 3.60 (t, J=7.9 Hz, 1H), 1.41 (d, J=10.5 Hz, 6H). Spectral data were in accordance with the literature.

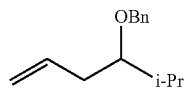

(((2-methylhex-5-en-3-yl)oxy)methyl)benzene prepared according to literature. See *Tetrahedron* 2011, 67, 5621-5629 ¹H NMR (500 MHz, CDCl₃) δ 7.38-7.31 (m, 4H), 7.30-7.24 (m, 1H), 5.89 (ddt, J=17.2, 10.2, 7.1 Hz, 1H), 5.10 (ddt, J=17.1, 2.2, 1.5 Hz, 1H), 5.05 (ddt, J=10.2, 2.2, 1.2 Hz, 1H), 4.58 (d, J=10 Hz, 1H), 4.50 (d, J=10 Hz, 1H), 3.20 (dt, J=6.2, 5.5 Hz, 1H), 2.31 (ddd, J=7.3, 5.8, 1.3 Hz, 2H), 1.95-1.80 (m, 1H), 0.96 (d, J=6.8 Hz, 3H), 0.93 (d, J=6.8 Hz, 3H). Spectral data were in accordance with the literature.

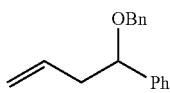

(1-(benzyloxy)but-3-en-1-yl)benzene prepared according to literature. See *Org. Lett.* 2010, 12, 2488-2491. ¹H NMR (500 MHz, CDCl₃) δ 7.41-7.27 (m, 10H), 5.78 (ddt, J=17.1, 10.2, 6.9 Hz, 1H), 5.07-5.00 (m, 2H), 4.47 (d, J=12.0 Hz, 1H), 4.37 (dd, J=7.6, 5.8 Hz, 1H), 4.27 (m, 1H), 2.65 (dddt, J=14.4, 7.7, 6.9, 1.3 Hz, 1H), 2.44 (dddt, J=14.2, 7.1, 5.8, 1.3 Hz, 1H). Spectral data were in accordance with the literature.

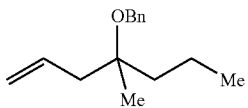 [SMILES: C=CCC(C)(CCC)OCc1ccccc1]

(((4-methylhept-1-en-4-yl)oxy)methyl)benzene

NaH (60 wt % dispersion in mineral oil, 600 mg, 15 mmol) was weighed into a flask with a stir bar. Dimethylacetamide (10 mL) was added to the vial and the mixture was cooled to 0° C., 4-Methylhept-1-en-4-ol (1.28 g, 10 mmol) was added slowly to the suspension. Benzyl bromide (1.4 mL, 12 mmol) was next added slowly to the reaction mixture. The reaction mixture was allowed to warm to room temperature and stirred overnight (ca. 10 h). The reaction mixture was diluted with water (ca. 125 mL) and extracted with diethyl ether (ca. 50 mL×3) and the combined organics were washed with brine and subsequently dried over MgSO4. Purification by column chromatography gave the desired compound (1.29 g, 59% yield) as a colorless oil. ¹H NMR (400 MHz, CDCl₃) δ 7.38-7.22 (m, 5H), 5.97-5.83 (m, 1H), 5.14-5.06 (m, 2H), 4.44 (s, 2H), 2.43-2.29 (m, 2H), 1.62-1.49 (m, 2H), 1.48-1.36 (m, 2H), 1.22 (s, 3H), 0.94 (t, J=7.2 Hz, 3H). ¹³C NMR (101 MHz, CDCl₃) δ 139.75, 134.63, 128.22, 127.26, 127.04, 117.18, 76.86, 63.23, 42.95, 40.42, 23.26, 16.71, 14.65. HRMS (EI⁺) calc'd for C₁₂H₁₂O (M-CH₂CHCH₂) 177.1279. found 177.1283.

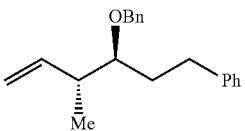 [SMILES: C=C[C@@H](C)[C@H](CCc1ccccc1)OCc1ccccc1]

(((1-allylcyclohexyl)oxy)methyl)benzene

Prepared according to the literature. See *Tetrahedron* 2011, 67, 5621-5629. ¹H NMR (500 MHz, CDCl₃) δ 7.40-7.36 (m, 2H), 7.36-7.31 (m, 2H), 7.28-7.23 (m, 1H), 5.98-5.80 (m, 1H), 5.12-5.04 (m, 2H), 4.42 (s, 2H), 2.34 (dt, J=7.2, 1.3 Hz, 2H), 1.87-1.81 (m, 2H), 1.69-1.56 (m, 3H), 1.50-1.43 (m, 2H), 1.42-1.32 (m, 2H), 1.32-1.20 (m, 1H). Spectral data were in accordance with the literature.

(trans-3-(benzyloxy)-4-methylhex-5-en-1-yl)benzene

NaH (60 wt % dispersion in mineral oil, 600 mg, 15 mmol) was weighed into a flask with a stir bar. Dimethylacetamide (10 mL) was added to the vial and the mixture, was cooled to 0° C. trans-4-methyl-1-phenylhex-5-en-3-ol (1.9 g, 10 mmol) was added slowly to the suspension. Benzyl bromide (1.4 mL, mmol) was next added slowly to the reaction mixture. The reaction mixture was allowed to warm to room temperature and stirred overnight (ca. 10 h).

The reaction mixture was diluted with water (ca. 125 mL) and extracted with diethyl ether (ca. 50 mL×3) and the combined organics were washed with brine and subsequently dried over MgSO$_4$. Purification by column chromatography gave the desired compound (1.47 g, 52% yield) as a colorless oil. $^1$H NMR (400 MHz, CDCl$_3$) δ 7.44-7.13 (m, 10H), 5.88-5.76 (m, 1H), 5.12-5.01 (m, 2H), 4.62 (d, J=10.1, 1H), 4.52 (d, J=10.1 1H), 3.35 (dt, J=8.4, 4.3 Hz, 1H), 2.84-2.76 (m, 1H), 2.60 (ddd, J=13.9, 9.8, 6.7 Hz, 2H), 1.88-1.70 (m, 2H), 1.05 (d, J=6.9 Hz, 3H). $^{13}$C NMR (126 MHz, CDCl$_3$) δ 142.45, 140.79, 138.87, 128.42, 128.33, 128.31, 127.81, 127.50, 125.69, 114.64, 82.11, 71.73, 40.16, 32.46, 32.23, 14.50. HRMS (EI$^+$) calc'd for C$_{20}$H$_{24}$O (M$^+$) 280.1827. found 280.1818.

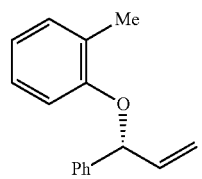 [SMILES: C=C[C@@H](Oc1ccccc1C)c1ccccc1]

(R)-1-phenyl-1-(2-methylphenoxy)-2-propene prepared according to the literature. See *J. Am. Chem. Soc.* 2003, 125, 3426-3427. $^1$H NMR (500 MHz, CDCl$_3$) δ 7.44-7.41 (m, 2H), 7.40-7.34 (m, 2H), 7.31-7.27 (m, 1H), 7.16-7.13 (m, 1H), 7.05 (tdd, J=8.0, 1.5, 0.9 Hz, 1H), 6.86-6.80 (m, 1H), 6.79 (d, J=8.2 Hz, 1H), 6.10 (ddd, J=17.1, 10.4, 5.8, Hz, 1H), 5.65 (d, J=5.8 Hz, 1H), 5.38 (d, J=17.3, Hz, 1H), 5.24 (dq, J=10.4, 1.2 Hz, 1H), 2.33 (s, 3H). Spectral data were in accordance with the literature. [α]D=−7.6 (c 0.94, CHCl$_3$), which is in accordance with literature values. 8 HPLC analysis indicated an enantiomeric excess of 95% [Chiralcel® OJ-H column, eluting with 99.9:0.1 hexane/i-PrOH, 0.7 mL/min, 220 nm; (S) enantiomer tR, 16.2, (R) enantiomer tR 16.7 min].

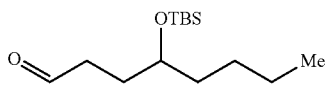 [SMILES: CCCCC(CCC=O)O[Si](C)(C)C(C)(C)C]

4-((tert-butyldimethylsilyl)oxy)octanal (Table 1, Entry 1)

98.6 mg (76% yield) obtained using procedure A. $^1$H NMR (500 MHz, CDCl$_3$) δ 9.79 (t, J=1.7 Hz, 1H), 3.71 (tt, J=6.2, 4.5 Hz, 1H), 2.49 (td, J=7.5, 1.7 Hz, 2H), 1.89-1.80 (m, 1H), 1.71 (dt, J=13.7, 6.9 Hz, 1H), 1.51-1.34 (m, 2H), 1.35-1.20 (m, 4H), 0.88, (m, 3H), 0.87 (s, 9H), 0.04 (d, J=4.1 Hz, 6H). Spectral data were in accordance with the literature. See *Org. Lett.* 2012, 14, 5728.

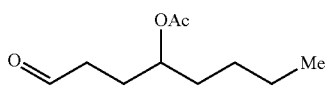 [SMILES: CCCCC(CCC=O)OC(C)=O]

1-oxooctan-4-yl acetate (Table 1, Entry 2)

70.8 mg (76% yield) obtained using procedure A. $^1$H NMR (500 MHz, CDCl$_3$) δ 9.76 (t, J=1.4 Hz, 1H), 4.89 (dddd, J=8.2, 7.3, 5.4, 4.0 Hz, 1H), 2.48 (ddt, J=8.2, 6.7, 1.3 Hz, 2H), 2.04 (s, 3H), 1.99-1.90 (m, 1H), 1.88-1.79 (m, 1H), 1.63-1.46 (m, 2H), 1.36-1.23 (m, 4H), 0.89 (t, J=7.0 Hz, 3H). $^{13}$C NMR (126 MHz, CDCl$_3$) δ 201.47, 170.82, 73.33, 39.96, 33.83, 27.40, 26.36, 22.50, 21.15, 13.94. HRMS (EI$^+$) calc'd for C8H15O2 (M-CH3CO) 143.1072. found 143.1109.

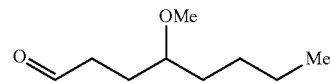 [SMILES: CCCCC(CCC=O)OC]

4-methoxyoctanal (Table 1, Entry 3)

71% obtained using procedure B.

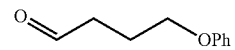

4-phenoxybutanal (Table 1, Entry 4)

72.0 mg (88% yield) obtained using procedure A. $^1$H NMR (500 MHz, CDCl$_3$) δ 9.85 (t, J=1.4 Hz, 1H), 7.32-7.24 (m, 2H), 6.95 (tt, J=7.4, 1.1 Hz, 1H), 6.88 (dt, J=7.8, 1.0 Hz, 2H), 4.01 (t, J=6.0 Hz, 2H), 2.68 (td, J=7.1, 1.3 Hz, 2H), 2.13 (tt, J=7.0, 6.0 Hz, 2H). Spectral data were in accordance with the literature. See *Angew. Chem. Int. Ed.* 2010, 49, 4047.

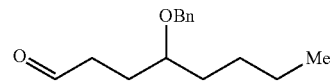 [SMILES: CCCCC(CCC=O)OCc1ccccc1]

4-(benzyloxy)octanal (Table 1, Entry 5)

99.9 mg (85% yield) obtained using procedure A. $^1$H NMR (500 MHz, CDCl$_3$) δ 9.76 (t, J=1.7 Hz, 1H), 7.40-7.26 (m, 5H), 4.54-4.50 (m, 1H), 4.45-4.41 (m, 1H), 3.41 (dtd, J=7.3, 6.0, 4.1 Hz, 1H), 2.52 (ddt, J=7.4, 6.9, 1.6 Hz, 2H), 1.92 (dddd, J=14.5, 7.6, 6.9, 4.1 Hz, 1H), 1.85-1.76 (m, 1H), 1.62 (dtd, J=13.6, 5.8, 4.7 Hz, 1H), 1.52-1.42 (m, 1H), 1.33 (ttd, J=6.0, 4.2, 3.2, 2.0 Hz, 4H), 0.91 (t, J=7.1 Hz, 3H). $^{13}$C NMR (126 MHz, CDCl$_3$) δ 202.55, 138.57, 128.36, 127.83, 127.57, 77.91, 70.87, 40.00, 33.34, 27.42, 26.28, 22.84, 14.06. HRMS (EI$^+$) calc'd for C15H22O2 (M+) 234.1620. found 234.1632.

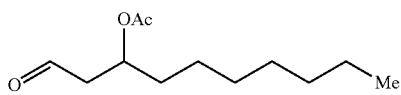 [SMILES: CCCCCCCC(CC=O)OC(C)=O]

1-oxodecan-3-yl acetate (Table 1, Entry 6)

75% obtained using procedure B.

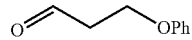

3-phenoxypropanal (Table 1, Entry 7)

61.3 mg (82% yield) obtained using procedure A. $^1$H NMR (500 MHz, CDCl$_3$) δ 9.76 (t, J=1.7 Hz, 1H), 7.32-7.27 (m, 2H), 7.00-6.95 (m, 1H), 6.93-6.90 (m, 2H), 4.32 (t, J=6.1 Hz, 2H), 2.91 (td, J=6.1, 1.6 Hz, 2H). Spectral data were in accordance with the literature. See *Tetrahedron: Asymmetry* 1999, 10, 3939.

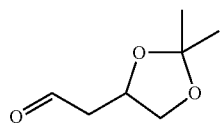

2-(2,2-dimethyl-1,3-dioxolan-4-yl)acetaldehyde (Table 1, Entry 8)

64% yield obtained using procedure B.

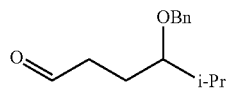

4-(benzyloxy)-5-methylhexanal (Table 2, Entry 1)

88.1 mg (80% yield) obtained using procedure A. $^1$H NMR (500 MHz, CDCl$_3$) δ 9.66 (t, J=1.7 Hz, 1H), 7.30-7.17 (m, 5H), 4.46 (d, J=12.5, 1H), 4.34 (d, J=12.5 1H), 3.11 (ddd, J=8.6, 5.4, 3.4 Hz, 1H), 2.43 (m, 2H), 1.90 (dtd, J=13.7, 6.9, 5.4 Hz, 1H), 1.78 (m, 1H), 1.70 (m, 1H), 0.89 (d, J=6.9 Hz, 3H), 0.85 (d, J=6.9 Hz, 3H). $^{13}$C NMR (126 MHz, CDCl$_3$) δ 202.68, 138.60, 128.35, 127.85, 127.57, 83.14, 71.64, 40.39, 30.27, 22.49, 18.72, 17.30. HRMS (EI$^+$) calc'd for C14H20O2 (M+) 220.1463. found 220.1466.

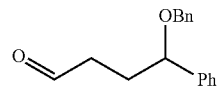 [SMILES: O=CCCC(OCc1ccccc1)c1ccccc1]

4-(benzyloxy)-4-phenylbutanal (Table 2, Entry 2)

94.1 mg (74% yield) obtained using procedure A. $^1$H NMR (500 MHz, CDCl$_3$) δ 9.74 (t, J=1.6 Hz, 1H), 7.35 (m, 10H), 4.47 (d, J=11.7 Hz, 1H), 4.37 (dd, J=8.3, 4.8 Hz, 1H), 4.25 (d, J=11.7 Hz, 1H), 2.54 (m, 2H), 2.14 (ddt, J=14.2, 8.4, 7.1 Hz, 1H), 2.04 (m, 1H). $^{13}$C NMR (126 MHz, CDCl$_3$) δ 202.21, 141.55, 138.18, 128.60, 128.38, 127.87, 127.81, 127.62, 126.63, 80.20, 70.52, 40.46, 30.91. HRMS (EI$^+$) calc'd for C11H13O2 (M-C$_6$H$_5$) 177.0916. found 177.0956.

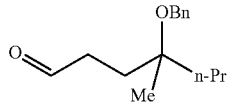

4-(benzyloxy)-4-methylheptanal (Table 2, Entry 3)

90.2 mg (77% yield) obtained using procedure A except NaNO$_2$ is replaced with AgNO$_2$ and the reaction is allowed to proceed for 24 h. Isolated as an inseparable mixture of aldehyde and ketone (9:1). Spectral data reported for aldehyde product (major). $^1$H NMR (500 MHz, CDCl$_3$) δ 9.79 (t, J=1.6 Hz, 1H), 7.35-7.31 (m, 4H), 7.28-7.24 (m, 1H), 4.37 (s, 2H), 2.55 (ddt, J=8.4, 6.7, 1.6 Hz, 2H), 1.99-1.92 (m, 1H), 1.89-1.80 (m, 1H), 1.60-1.50 (m, 2H), 1.43-1.35 (m, 2H), 1.23 (s, 3H), 0.95 (t, J=7.3 Hz, 3H). $^{13}$C NMR (126 MHz, CDCl$_3$) δ 202.66, 139.36, 128.30, 127.23, 127.19, 76.23, 63.25, 40.66, 38.73, 30.32, 23.02, 17.04, 14.69. HRMS (EI$^+$) calc'd for C13H19O (M-CH$_2$CHO) 191.1436. found 191.1444.

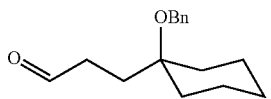 [SMILES: O=CCCC1(OCc2ccccc2)CCCCC1]

3-(1-(benzyloxy)cyclohexyl)propanal 94.8 mg (77% yield) obtained using procedure A except NaNO$_2$ is replaced with AgNO$_2$ and the reaction is allowed to proceed for 24 h. $^1$H NMR (500 MHz, CDCl$_3$) δ 9.81 (t, J=1.4 Hz, 1H), 7.38-7.32 (m, 4H), 7.29-7.24 (m, 1H), 4.35-4.29 (s, 2H), 2.54 (ddd, J=9.1, 6.5, 1.5 Hz, 2H), 1.87 (m, 4H), 1.63 (m, 3H), 1.48 (m, 2H), 1.32 (m, 3H). $^{13}$C NMR (101 MHz, CDCl$_3$) δ 202.58, 139.30, 128.31, 127.23, 127.18, 74.77, 62.24, 37.90, 34.45, 28.51, 25.85, 21.92. HRMS (EI$^+$) calc'd for C16H22O2 (M+) 246.1620. found 246.1618.

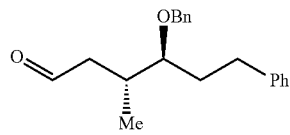 [SMILES: C[C@H](CC=O)[C@H](CCc1ccccc1)OCc1ccccc1]

trans-4-(benzyloxy)-3-methyl-6-phenylhexanal 96.3 mg (65% yield) obtained using procedure A except NaNO2 is replaced with AgNO2 and the reaction is allowed to proceed for 24 h. $^1$H NMR (500 MHz, CDCl$_3$) δ 9.72 (t, J=2.1 Hz, 1H), 7.38-7.14 (m, 10H), 4.55-4.48 (m, 2H), 3.26 (td, J=6.1, 4.3 Hz, 1H), 2.77 (ddd, J=13.7, 9.9, 6.0 Hz, 1H), 2.66 (ddd, J=13.8, 10.0, 6.7 Hz, 1H), 2.50-2.43 (m, 2H), 2.34-2.26 (m, 1H), 1.90-1.81 (m, 2H), 1.00 (d, J=6.7 Hz, 3H). $^{13}$C NMR (126 MHz, CDCl$_3$) δ 202.07, 142.18, 138.39, 128.43, 128.39, 128.34, 127.92, 127.66, 125.86, 82.08, 71.66, 47.86, 32.27, 31.27, 31.06, 16.36. HRMS (EI$^+$) calc'd for C20H24O2 (M+) 296.1776. found 296.1778.

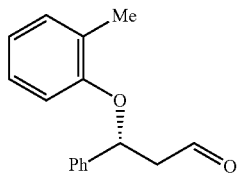 [SMILES: Cc1ccccc1O[C@H](CC=O)c1ccccc1]

(R)-3-phenyl-3-(2-methylphenoxy)propanal 85.3 mg (71% yield) obtained using procedure A except NaNO$_2$ is replaced with AgNO$_2$. $^1$H NMR (500 MHz, CDCl$_3$) δ 9.88 (dd, J=2.5, 1.6 Hz, 1H), 7.41-7.33 (m, 4H), 7.32-7.27 (m, 1H), 7.13 (ddd, J=7.4, 1.7, 0.9 Hz, 1H), 6.98 (td, J=8.1, 1.7 Hz, 1H), 6.82 (td, J=7.4, 1.1 Hz, 1H), 6.65 (dd, J=8.1, 1.2 Hz, 1H), 5.72 (dd, J=8.6, 4.2 Hz, 1H), 3.15 (ddd, J=16.6, 8.6, 2.6 Hz, 1H), 2.88 (ddd, J=16.6, 4.2, 1.6 Hz, 1H), 2.28 (s, 3H). $^{13}$C NMR (126 MHz, CDCl$_3$) δ 199.83, 155.38, 140.36, 130.77, 128.91, 128.06, 127.16, 126.58, 125.67, 120.88, 112.88, 74.88, 51.91, 16.42. HRMS (EI$^+$) calc'd for C$_{16}$H$_{16}$O$_2$ (M+) 240.1150. found 240.1155. [α]D=−10.1 (c 0.48, CHCl$_3$). Enantiomeric excess checked by derivatization to atomoxetine (vide infra).

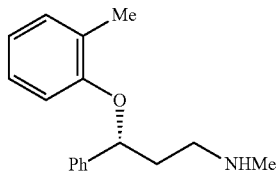 [SMILES: CNCC[C@@H](Oc1ccccc1C)c1ccccc1]

(R)-3-phenyl-3-(2-methylphenoxy)propanal was derivatized to atomoxetine by treatment of the aldehyde with excess NaBH$_3$CN (ca. 3 equiv) and methylamine hydrochloride (ca. 50 equiv) to provided a crude mixture (37% yield of atomoxetine according to $^1$H NMR analysis), which was purified by preparatory thin layer chromatography for characterization and determination of enantiomeric excess. $^1$H NMR (500 MHz, CDCl$_3$) δ 7.37-7.29 (m, 4H), 7.27-7.22 (m, 1H), 7.12 (ddd, J=7.3, 1.7, 0.9 Hz, 1H), 6.98-6.92 (m, 1H), 6.78 (td, J=7.4, 1.1 Hz, 1H), 6.62-6.58 (m, 1H), 5.28 (dd, J=8.3, 4.4 Hz, 1H), 2.90-2.80 (m, 2H), 2.47 (s, 3H), 2.32 (s, 3H), 2.30-2.19 (m, 1H), 2.11 (dtd, J=14.2, 7.3, 4.5 Hz, 1H). Spectral data were in accordance with the literature. [α]D=−31.6 (c 0.10, CHCl$_3$), which is in accordance with literature values. See *Tetrahedron: Asymmetry* 2013, 24, 913-918. SFC analysis indicated an enantiomeric excess of 94% [Chiralcel® OD-H column, eluting with 20% MeOH, 2.5 mL/min, 220 nm; (S) enantiomer tR, 3.95, (R) enantiomer tR 5.4 min]

Example 5

Transformations of Aldehydes to Other Functional Groups

The new oxidation conditions described, using AgNO$_2$, could be used to generate aldehyde precursors that can undergo subsequent transformation.

Example 5.1

Testing Functional Group Compatibility

In a series of experiments, terminal aldehydes were generated in situ and subsequently hydroaminated to offer an entry into the anti-Markovnikov hydroamination of aliphatic olefins. As shown in Table 7, hydroamination of 4-phenyl-1-butene (1k) with N-methylaniline (2a) furnished adduct 3k in 64% yield (Table 7, entry 1). Anti-Markovnikov hydroamination of 1-dodecene (1m), a transformation that notably cannot be substrate-controlled, proceeded in 40% yield to provide 3p (entry 3). The more sterically demanding allyl cyclohexane (1n) also proved to be a good substrate (entry 4), delivering 3r in 56% yield. Examination of the substrate scope revealed that this transformation could accommodate a variety of functional groups, including nitro (entry 2), ester (entry 5), alkyl halide (entry 6), and aryl halide (entry 7) groups. To the best of the inventors' knowledge, this methodology represents the first metal-catalyzed approach to the intermolecular anti-Markovnikov hydroamination of an unbiased olefin with an aryl amine. Furthermore, it should be noted that this catalytic system allows access to elusive linear amine adducts through a one-pot technique, thus avoiding isolation of less stable aldehyde intermediates.

TABLE 7

Hydroamination of aliphatic olefins with N-methylaniline i. PdCl$_2$(PhCN)$_2$ (12 mol %)
CuCl$_2$·2H$_2$O (12 mol %)
AgNO$_2$ (6 mol %)
t-BuOH, MeNO$_2$, O$_2$, rt

R⟶ 1 ii. N—Me aniline (2a, 2.5 equiv)
10 (10 mol %)
5:2 formic acid/TEA azeotrope
argon, 85 °C.

R⟶NMePh 3k, p-u

| Entry | Substrate | Product | Yield$^a$ |
|---|---|---|---|
| 1 | 1k (4-phenyl-1-butene) | 3k | 64% |
| 2 | 11 (O$_2$N-(CH$_2$)$_3$-CH=CH$_2$) | 3p | 65% |
| 3 | 1m (CH$_3$-(CH$_2$)$_9$-CH=CH$_2$) | 3q | 40% |
| 4 | 1n (allyl cyclohexane) | 3r | 56% |
| 5 | 1o (MeO-C(O)-(CH$_2$)$_8$-CH=CH$_2$) | 3s | 60% |
| 6 | 1p (Br-(CH$_2$)$_5$-C(O)-CH=CH$_2$) | 3t | 39% |
| 7 | 1q (2-bromophenyl propene) | 3u | 46% |

TABLE 7-continued

Hydroamination of aliphatic olefins with N-methylaniline

i. PdCl$_2$(PhCN)$_2$ (12 mol %)
CuCl$_2$•2H$_2$O (12 mol %)
AgNO$_2$ (6 mol %)
t-BuOH, MeNO$_2$, O$_2$, rt
ii. N—Me aniline (2a, 2.5 equiv)
10 (10 mol %)
5:2 formic acid/TEA azeotrope
argon, 85 °C.

| Entry | Substrate | Product | Yield[a] |
|-------|-----------|---------|----------|

[a]Yield determined by isolation (0.6 mmol scale).

Example 5.2

Chiral Substrates

A catalyst-controlled anti-Markovnikov Wacker oxidation combined with established enantioselective methodologies enables a powerful strategy to access versatile enantioenriched building blocks. To demonstrate the utility of this synthetic approach, atomoxetine, a norepinephrine re-uptake inhibitor approved for the treatment of attention deficit disorder, was targeted (Scheme 2).

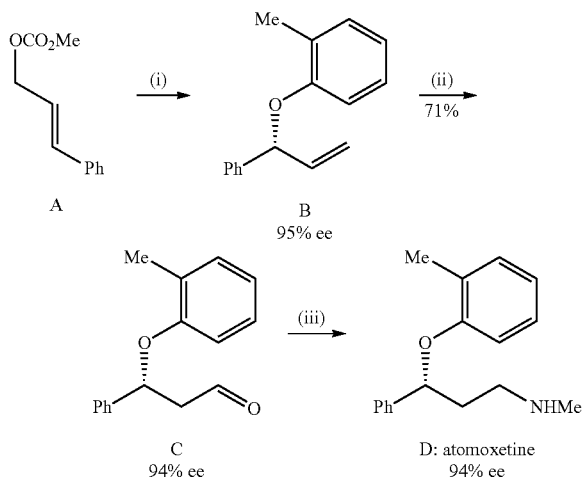

Scheme 2. Synthesis of Atomoxetine[a]

[a](i) [Ir(COD)Cl]$_2$ (1 mol %), (R,R,R)-(3,5-dioxa-4-phospha-cyclohepta[2,1-a;3,4-a']dinaphthalen-4-yl)bis(1-phenylethyl)amine (2 mol %), THF, 50° C., 16 h; (ii) PdCl$_2$(PhCN)$_2$ (10%), CuCl$_2$•2H$_2$O (10%), AgNO$_2$ (5%), t-BuOH/MeNO$_2$ (15:1), O$_2$ (1 atm), rt, 5 h; (iii) NaBH$_3$CN (2 equiv), MeNH$_3$Cl (excess), rt, 24 h.

At the outset, one potential concern with this approach was whether the stereocenter proximal to the alkene would racemize under the nitrite-modified reaction conditions. To test the viability of this route, cinnamyl alcohol derivative A was transformed into chiral allylic ether B via a highly enantioselective iridium-catalyzed allylic substitution reaction. See López, F.; et al., *J. Am. Chem. Soc.* 2003, 125, 3426-3427 for method employed. Upon treatment of B using an embodiment of the invention, the corresponding aldehyde, C, was produced in good yield. Subsequent derivatization via reductive amination demonstrated that the targeted drug, D, could be accessed without loss of enantiopurity over the course of the synthetic sequence. The success of this strategy, particularly the retention of stereochemical information at the allylic position, showcases that the nitrite-modified Wacker oxidation is compatible with well-established asymmetric methods and provides access to valuable synthetic products in a modular, catalytic manner.

As those skilled in the art will appreciate, numerous modifications and variations of the present invention are possible in light of these teachings, and all such are contemplated hereby. For example, in addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, each in its entirety, for all purposes.

What is claimed:

1. A method comprising contacting a terminal olefin with a Wacker-type oxidation catalyst system mixture comprising:
   (a) a dichloro-bis(nitrile) palladium (II) complex; and
   (b) copper chloride, either as CuCl or CuCl$_2$;
   said Wacker-type oxidation catalyst system mixture further comprising
   (c) an inorganic nitrite salt;
   said contacting done in the presence of a tertiary alcohol under aerobic reaction conditions sufficient to convert at least a portion of the terminal olefin to an aldehyde, such that the selectivity for aldehyde is at least 50%.

2. The method of claim 1, wherein the inorganic nitrite salt comprises silver nitrite.

3. The method of claim 1, wherein the inorganic nitrite salt comprises NaNO$_2$ or AgNO$_2$.

4. The method of claim 1, wherein the dichloro-bis(nitrile) palladium (II) complex comprises bis(benzonitrile)dichloro-palladium(II).

5. The method of claim 1, wherein the tertiary alcohol comprises tert-butanol.

6. The method of claim 5, wherein the the Wacker-type oxidation catalyst system mixture further comprises nitromethane.

7. The method of claim 1, wherein the terminal olefin has a structure of Formula (1):

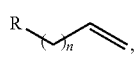

wherein:
n=2 to 9; and
R is optionally halogenated benzyl, optionally halogenated phenyl, carboxy acid, carboxy acid ester, cyclohexyl, halogen, —O—C$_{1-12}$-alkyl, hydroxyl, or nitro.

8. A method of converting a terminal olefin to an acetal, acylal, terminal alcohol, α, β-unsaturated aldehyde, aldoxime, anhydride, amide, amine, α-amino nitrile, carboxylic acid, carboxylate ester, α, β-unsaturated carboxylic acid, 1, 3 diol, epoxide, α, β-unsaturated epoxy ester, β-hydroxyester, α-hydroxy nitrile, hydrazone, nitrile, β-nitro alcohol, semicarbazone, halide, gem-dihalide, or α-halo ether, said method comprising:
  (a) converting the terminal olefin to a aldehyde according to the method of claim 1; and
  (b) converting the aldehyde to the acetal, acylal, terminal alcohol, α, β-unsaturated aldehyde, aldoxime, anhydride, amide, amine, α-amino nitrile, carboxylic acid, carboxylate ester, α, β-unsaturated carboxylic acid, 1, 3 diol, epoxide, α, β-unsaturated epoxy ester, β-hydroxyester, α-hydroxy nitrile, hydrazone, nitrile, β-nitro alcohol, semicarbazone, halide, gem-dihalide, or α-halo ether.

9. The method of claim 1, wherein the molar ratio of the dichloro-bis(nitrile) palladium(II) complex to the copper chloride is about 1:1.

10. The method of claim 1, wherein the molar ratio of the dichloro-bis(nitrile) palladium(II) complex to the inorganic nitrite salt is about 2:1.

11. The method of claim 1, wherein the Wacker-type oxidation catalyst system mixture comprises:
  (a) bis(benzonitrile)dichloro-palladium(II); and
  (b) copper chloride; and wherein
the Wacker-type oxidation catalyst system mixture further comprises
  (c) sodium nitrite or silver nitrite.

12. The method of claim 11, wherein the Wacker-type oxidation catalyst system mixture further comprises tert-butanol.

13. The method of claim 12, wherein the Wacker-type oxidation catalyst system mixture further comprises nitromethane.

14. The method of claim 11, wherein the molar ratio of the bis(benzonitrile)dichloro-palladium(II) to the copper chloride complex is about 1:1.

15. The method of claim 11, wherein the molar ratio of the bis(benzonitrile)dichloro-palladium(II) to the inorganic nitrite salt is about 2:1.

* * * * *